(12) United States Patent
Farahmand et al.

(10) Patent No.: US 10,729,382 B2
(45) Date of Patent: Aug. 4, 2020

(54) METHODS AND SYSTEMS TO PREDICT A STATE OF THE MACHINE USING TIME SERIES DATA OF THE MACHINE

(71) Applicant: Mitsubishi Electric Research Laboratories, Inc., Cambridge, MA (US)

(72) Inventors: Amir massoud Farahmand, Cambridge, MA (US); Daniel Nikolaev Nikovski, Brookline, MA (US)

(73) Assignee: Mitsubishi Electric Research Laboratories, Inc., Cambridge, MA (US)

( * ) Notice: Subject to any disclaimer, the term of this patent is extended or adjusted under 35 U.S.C. 154(b) by 0 days.

(21) Appl. No.: 15/382,857

(22) Filed: Dec. 19, 2016

(65) Prior Publication Data

US 2018/0168515 A1  Jun. 21, 2018

(51) Int. Cl.
| | | |
|---|---|---|
| *G16H 50/30* | (2018.01) | |
| *A61B 5/00* | (2006.01) | |
| *G06N 5/04* | (2006.01) | |
| *G16H 50/50* | (2018.01) | |
| *G06N 20/00* | (2019.01) | |

(52) U.S. Cl.
CPC .......... *A61B 5/7267* (2013.01); *A61B 5/725* (2013.01); *A61B 5/7275* (2013.01); *G06N 5/04* (2013.01); *G06N 20/00* (2019.01); *G16H 50/30* (2018.01); *G16H 50/50* (2018.01)

(58) Field of Classification Search
None
See application file for complete search history.

(56) References Cited

U.S. PATENT DOCUMENTS

| | | | | |
|---|---|---|---|---|
| 5,914,882 A | * | 6/1999 | Yeghiazarians | F16P 3/00 408/1 R |
| 2006/0036403 A1 | * | 2/2006 | Wegerich | G05B 23/0254 702/183 |
| 2008/0024615 A1 | * | 1/2008 | Alvarez | H04N 5/232 348/211.7 |
| 2008/0052027 A1 | * | 2/2008 | Witter | H02J 13/0079 702/108 |
| 2009/0165086 A1 | * | 6/2009 | Trichina | G06F 7/588 726/2 |

(Continued)

*Primary Examiner* — Bilkis Jahan
(74) *Attorney, Agent, or Firm* — Gennadiy Vinokur; James McAleenan; Hironori Tsukamoto

(57) ABSTRACT

Systems and methods for determining a model for predictive inference on an operation of a machine. A processor is configured to acquire time series data, the times series data includes training data and test data, the time series data represents an operation of the machine for a period of time, and the training data includes observations labeled with an outcome of the predictive inference. Apply recursive and stable filters for filtering at a training time, at a test time or both, such that a data point in the filtered time series data corresponds to an observation in the time series data that is a function of the corresponding observation and past observations in the time series data preceding the corresponding observation. Determine the model for the predictive inference using the training data, based on filtering the training data with filters to produce filtered time series data, and store in memory.

19 Claims, 26 Drawing Sheets

(56) References Cited

U.S. PATENT DOCUMENTS

| | | | | |
|---|---|---|---|---|
| 2011/0200229 A1* | 8/2011 | Tuzel | ................... | H04N 19/597 |
| | | | | 382/103 |
| 2012/0290230 A1* | 11/2012 | Berges Gonzalez | ... | G01D 4/004 |
| | | | | 702/61 |
| 2015/0097970 A1* | 4/2015 | Zeng | .................... | H04N 17/004 |
| | | | | 348/192 |

* cited by examiner

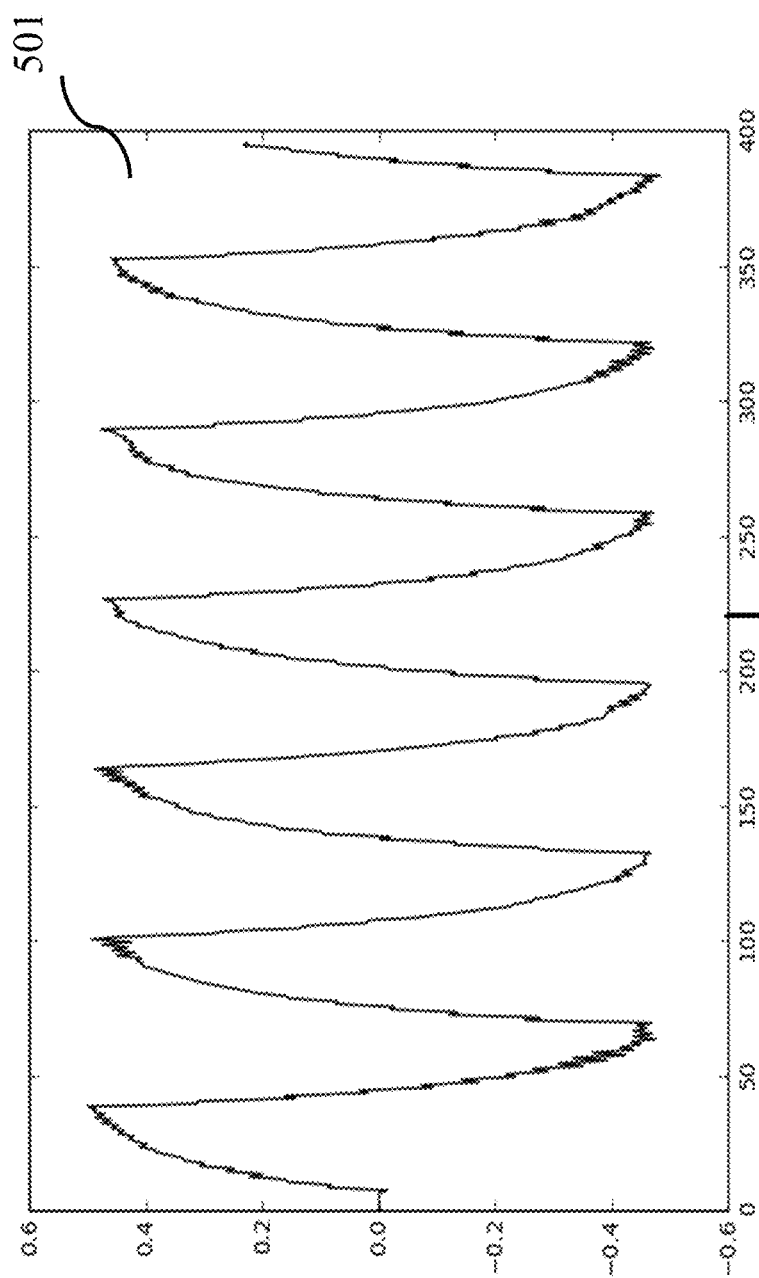

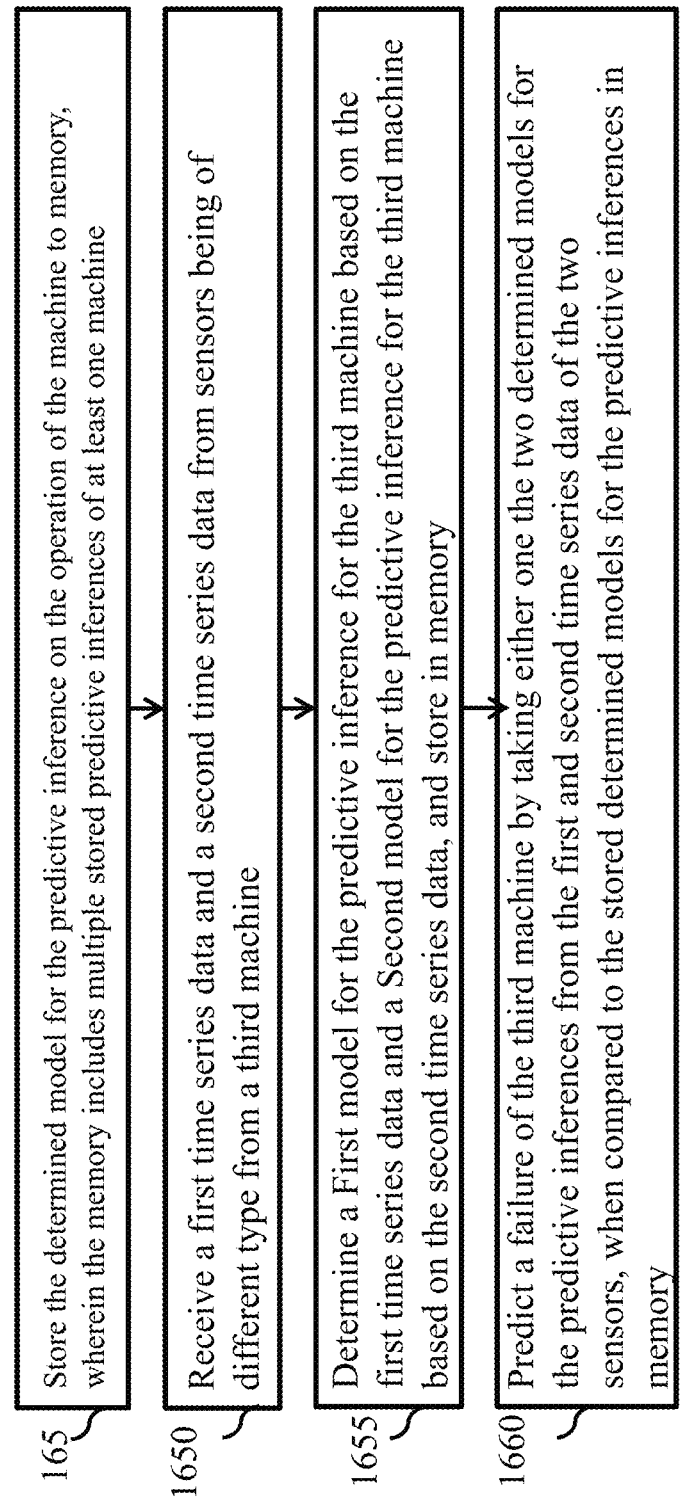
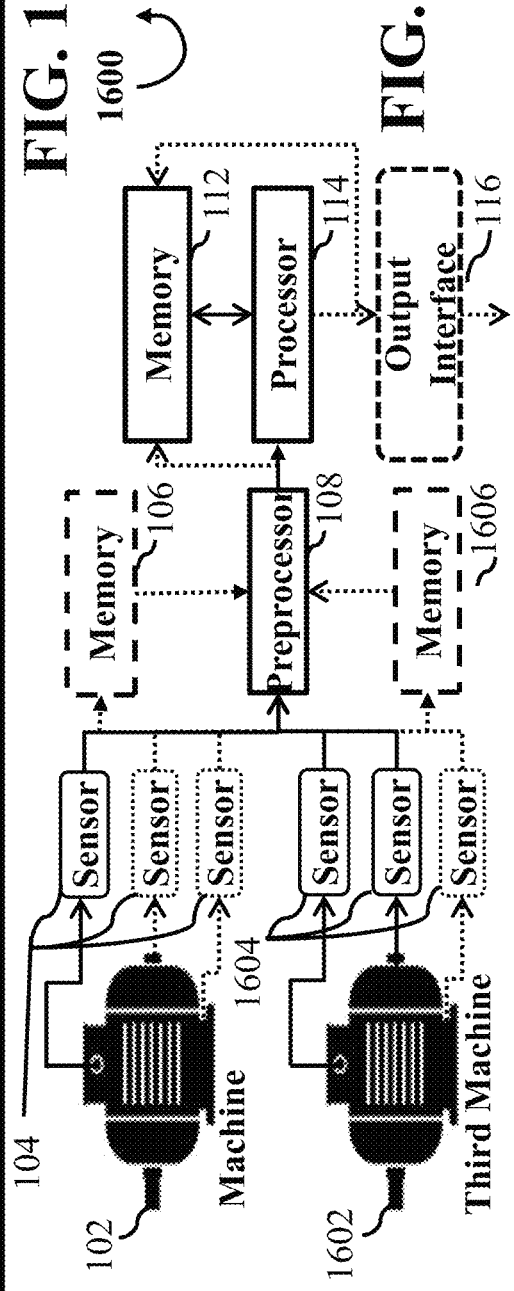

METHODS AND SYSTEMS TO PREDICT A STATE OF THE MACHINE USING TIME SERIES DATA OF THE MACHINE

FIELD

The present disclosure relates generally to determining a model for a predictive inference on an operation of a machine, and in particular, the use of time series data of the machine to provide an approximate state of the machine.

BACKGROUND

Modern computer systems collect large amounts of information from various physical systems. These physical machines are usually subjected to repetitive loads organized in regular duty cycles, and tend to wear out in a more or less regular pattern, gradually reaching a state when they fail, due to a partial or complete breakdown. Maintaining such machines in good working order is an important task associated with their operation, and how and when maintenance is performed has a very significant effect on the economic aspect of their operation. One maintenance strategy is to repair a machine only after it fails or termed as corrective maintenance. The strategy of corrective maintenance is very often not optimal at all, because repairs of an entire failed machine might be costlier than replacing a single part before the machine breaks, and also machine failure might result in wasted materials, unacceptable product quality, and might even endanger the personnel operating the machine. In situations when corrective maintenance is not a viable or economic option, a different strategy is used, such as regular maintenance of the machine at fixed periodic intervals, for example once month or year. Examples of such safety critical machines are elevators and cars, wherein maintenance is done once per year, and corresponding certificates, which is known as preventive maintenance.

Although preventive maintenance addresses the safety issues that are associated with machine maintenance, there are many cases when it is not economically optimal. The first problem with preventive maintenance is that the length of the maintenance cycle is often arbitrary (e.g., one year or one month), and has more to do with the convenience of the inspection authorities and the logistics of the inspection process (e.g. issuing inspection stickers for cars), than with the actual need of the machines. The second problem is that a single maintenance cycle could not possibly be optimal for all machines in a group, where some of the machines are new, and might require maintenance not very often, whereas older machines might require maintenance much more often.

In the machine analysis industry, sensors are typically used to measure machine parameters. As the instrumentation of machine operations increases, large amounts of data are being collected from sensors that monitor operations of the machines. The data from some sensors may also be generated at a relatively high frequency, which further results in large amounts of data. However, having to use large amounts of data presents computational challenges regarding cost and time, and even then it is possible the expected result may not provide a good representation of the real state of the system or machine.

Therefore, a need exists in the art for an improved way to detect and/or predict machine failure from the large amounts of data.

SUMMARY

Embodiments of the present disclosure relates generally to determining a model for a predictive inference on an operation of a machine, and in particular, the use of time series data of the machine to provide an approximate state of the machine such as predicting the failure of the machine.

Some embodiments of present disclosure are based on a realization that times series data generated from sensors in communication with a machine, can be filtered using a set of recursive and stable filters at a training time, at a test time or both, to obtain a set of filtered time series data. Wherein each data point in the filtered time series data corresponds to an observation in the times series data that is a function of all previous observations. In other words, each data point carries information about potentially all past observations.

The initial problem to overcome is trying to obtain a predictive inference from time series data based on a dynamic state of the machine, or that the machine's state changes over time, when the predictive inferences are unknown, and when there are only observations related to the state of the machine are being measured. To better understand the problem, let's assume we want to determine a state of a sinusoidal wave (which is figuratively a predictive inference of the machine), wherein there is only one observation of the sinusoidal wave to make the determination of the state of the sinusoidal wave. However, because the sinusoidal wave underlying dynamical system is linear and two dimensional, two consecutive observations of the sinusoidal wave are required, thus, one observation is not enough. Which means, there is no solution to the problem for determining the state of a sinusoidal wave, because there not enough information, i.e. only one observation is available, and there needs to be two observations to solve the problem.

In other words, if a set of observations corresponds uniquely to the state of the machine, then machine learning methods may be used to design various predictors, i.e. predictive inferences. However, the sensory data at each time instance may not provide enough information about the actual state of the machine. The number of the required observations depends on the dimensionality d of the system/machine, i.e., d for linear and 2d+1 for non-linear systems/machines. If the information vector does not include enough observations, then the machine learning methods fail.

However, we realized that by filtering time series data with a recursive and stable filters, each data point in the filtered time series data corresponds to an observation in the times series data is a function of all previous observations. In such a manner, each data point carries information about possibly all past observations. In other words, we discovered how to obtain more information about the actual state of the machine, in order for the machine learning methods to be able used to design the various predictors, i.e. predictive inferences. Moreover, through experimentation we learned that the training data can be filtered with multiple random filters to produce a set of filtered data. The data points from different filtered data that correspond to the same observation have the same label and can form the informational vector used in the machine learning methods. Wherein a number of filters defines a size of the informational vector.

Based upon our realization, we can determine a model for a predictive inference on an operation of a system/machine, by using a number of filters to provide an approximate state of the system/machine. Further, if the number of filters are increased, then so also is the quality of the approximation or prediction. Wherein, the output of these filters can be the input of another machine learning module that predicts the next state of the system/machine, or the type of fault, or remaining useful life. Thus, we have overcome problem of not being able to extract enough suitable state representation from the time series data, to approximately summarize a times series generated by an unknown dynamical system, i.e., the machine.

Before solving a machine learning problem, given using the time series data, first an initial determination needs to be made, as what problem is to be solved? For example, is the problem being solved for: (1) determining a predictive inference or probability of failure given the time series data (survival analysis); (2) determining a fault diagnosis (classification); or (3) determining a remaining useful life (regression). Secondly, there needs to be a determination as to how to extract information available in the time series data? Upon knowing the answers to the above two questions, and given using time series data, we can begin.

For example, some embodiments of the present disclosure begin determining a model for predictive inference on an operation of a machine, i.e. the machine learning problem, by the step of accessing time series data stored in a memory. Wherein, the times series data includes training time series data and test time series data, and the time series data represents an operation of the machine for a period of time, and the training times series data includes observations labeled with an outcome of the predictive inference.

The next step is to apply a set of recursive and stable filters for filtering at a training time, at a test time or both, to the times series data to obtain a set of filtered time series data. Such that a data point in the set of filtered time series data corresponds to an observation in the time series data that is a function of the corresponding observation and past observations in the time series data preceding the corresponding observation. Remember, based on our realization, we discovered how to obtain more information about the actual state of the machine, in particular, that the training data can be filtered with multiple random filters to produce a set of filtered data. Such that the data points from the set of filtered data that correspond to the same observation, have the same label and can form an informational vector used in the machine learning methods, i.e. that the number of filters defines a size of the informational vector.

The next step includes determining the model for the predictive inference using the training time series data, based on filtering the training time series data with a set of filters to produce a set of filtered training time series data, so as to obtain the determined model for the predictive inference.

The determined model for the predictive inference can be stored in memory or outputted via the output interface to be an input of another machine learning method/module that predicts a next state of the machine, or a type of fault, or a remaining useful life.

According to an embodiment of the present disclosure, a system for determining a model for predictive inference on an operation of a machine. The system includes sensors in communication with the machine, an output interface and a processor. The processor is in communication with a non-transitory computer storage medium, and is configured to first access time series data generated by the sensors in communication with the machine stored in the non-transitory computer storage medium, or acquire the time series data via an input interface in communication with a processor. Wherein the times series data includes training time series data and test time series data, such that the time series data represents an operation of the machine for a period of time, and the training times series data includes observations labeled with an outcome of the predictive inference. Next, is to apply a set of recursive and stable filters for filtering at a training time, at a test time or both, to the times series data to obtain a set of filtered time series data. Wherein a data point in the set of filtered time series data corresponds to an observation in the time series data that is a function of the corresponding observation and past observations in the time series data preceding the corresponding observation. Further, determine the model for the predictive inference using the training time series data, based on filtering the training time series data with a set of filters to produce a set of filtered training time series data, so as to obtain the determined model for the predictive inference. Finally, store the determined model for the predictive inference on the operation of the machine to the non-transitory computer storage medium or output the determined model via the output interface in communication with the processor.

According to another embodiment of the present disclosure, a method for assessing the health of a machine or a living organism having electrical activity by determining a model for predictive inference on an operation of a machine or the living organism. The method includes accessing stored time series data generated by the sensors in communication with the machine or the living organism from a computer readable memory. The times series data includes training time series data and test time series data, wherein the time series data represents an operation of the machine or the living organism, for a period of time, and the training times series data includes observations labeled with an outcome of the predictive inference. Then, applying a set of recursive and stable filters for filtering at a training time, at a test time or both, to the times series data to obtain a set of filtered time series data. Such that a data point in the set of filtered time series data corresponds to an observation in the time series data that is a function of the corresponding observation and past observations in the time series data preceding the corresponding observation. Wherein the filtering at the training time uses the training times series data for the filtering and the filtering at the test time uses the test time series data for the filtering. Next, determining the model for the predictive inference using the training time series data, based on filtering the training time series data with a set of filters to produce a set of filtered training time series data, so as to obtain the determined model for the predictive inference. Finally, storing the determined model for the predictive inference on the operation of the machine or the living organism to the computer readable memory, or outputting the determined model via an output interface in communication with the processor According to another embodiment of the present disclosure, a non-transitory computer readable storage medium embodied thereon a program executable by a computer for performing a method, the method is for assessing the health of a machine, by determining a model for predictive inference on an operation of the machine. The method including using stored time series data generated by sensors in communication with the machine from the non-transitory computer storage medium. Wherein the times series data includes training time series data and test time series data, wherein the time series data represents an operation of the machine for a period of time, and the training times series data includes observations labeled with an outcome of the predictive inference. Next, applying a set of recursive and stable filters for filtering at a training time, at a test time or both, to the times series data to obtain a set of filtered time series data. Such that a data point in the set of filtered time series data corresponds to an observation in the time series data that is a function of the corresponding observation and past observations in the time series data preceding the corresponding observation. Wherein the filtering at the training time uses the training times series data for the filtering and the filtering at the test time uses the test time series data for the filtering. Then, determining the model for the predictive inference using the training time series data, based on filtering the training time series data with a set of filters to produce a set of filtered training time series data, so as to obtain the determined model for the predictive inference. Finally, storing the determined model for the predictive inference on the operation of the machine to the non-transitory computer storage medium or outputting the determined model via an output interface in communication with the processor.

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

FIG. 5A, FIG. 5B and FIG. 5C are graphs illustrating the multitude output time series of the random projection filter bank given the input time series, according to embodiments of the present disclosure;

FIG. 16A is a block diagram illustrating the steps of another embodiment incorporating a first times series data and a second time series data from sensors of a third machine to determine two new models for predictive inferences for the third machine, and using the previously stored determined models for the predictive inferences, compared to the two new determined models for the predictive inferences of the third machine, to predict a failure of the third machine, according to an embodiment of the present disclosure;

FIG. 16B is a schematic illustrating components of the system of FIG. 16A, according to an embodiment of the present disclosure.

Figure 1A:
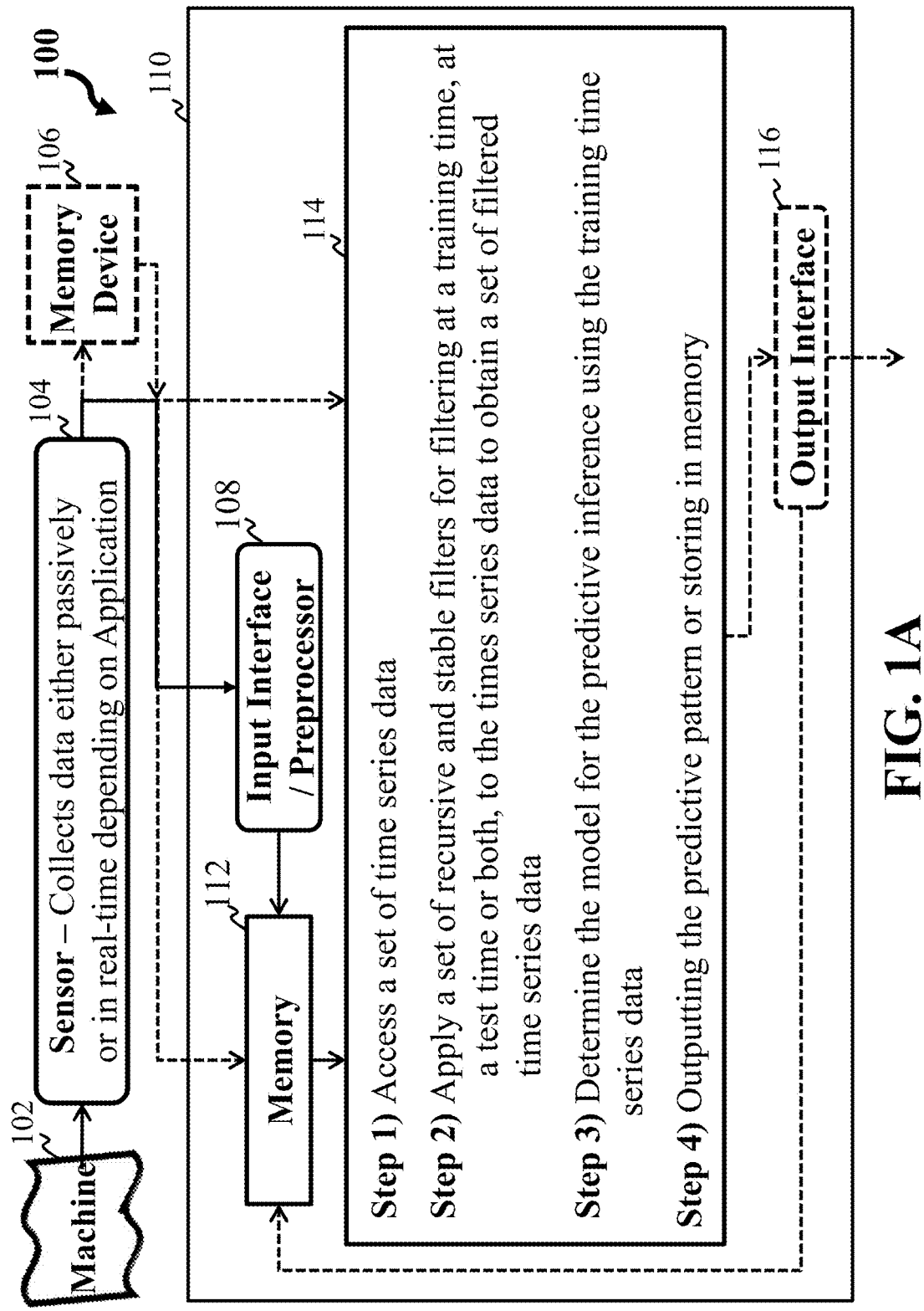
FIG. 1A is a block diagram illustrating the system for determining a model for a predictive inference on an operation of a machine, according to an embodiment of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. Contemplated are various changes that may be made in the function and arrangement of elements without departing from the spirit and scope of the subject matter disclosed as set forth in the appended claims.

Specific details are given in the following description to provide a thorough understanding of the embodiments. However, understood by one of ordinary skill in the art can be that the embodiments may be practiced without these specific details. For example, systems, processes, and other elements in the subject matter disclosed may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Also, individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but may have additional steps not discussed or included in a figure. Furthermore, not all operations in any particularly described process may occur in all embodiments. A process may correspond to a method, a function, a procedure, a subroutine, a subprogram, etc. When a process corresponds to a function, the function's termination can correspond to a return of the function to the calling function or the main function.

Furthermore, embodiments of the subject matter disclosed may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Definition of Terms

According to the definition of terms with regard to the present disclosure, the term predictive inference refers to the task of prediction of the current or future state of a machine based on data observed in the form of a time series, such as whether it is faulty or not, or when the fault might happen. The term model selection procedure refers to a procedure that compares several candidate predictors and selects the one that has the best predictive performance. The predictive performance is evaluated based on a subset of training time series. The term observation refers to the data measured from a machine using various sensors. The term label refers to the outcome of a predictive inference task such as the type of fault, or the time of failure.

Overview of Embodiments of the Present Disclosure

Figure 1B:
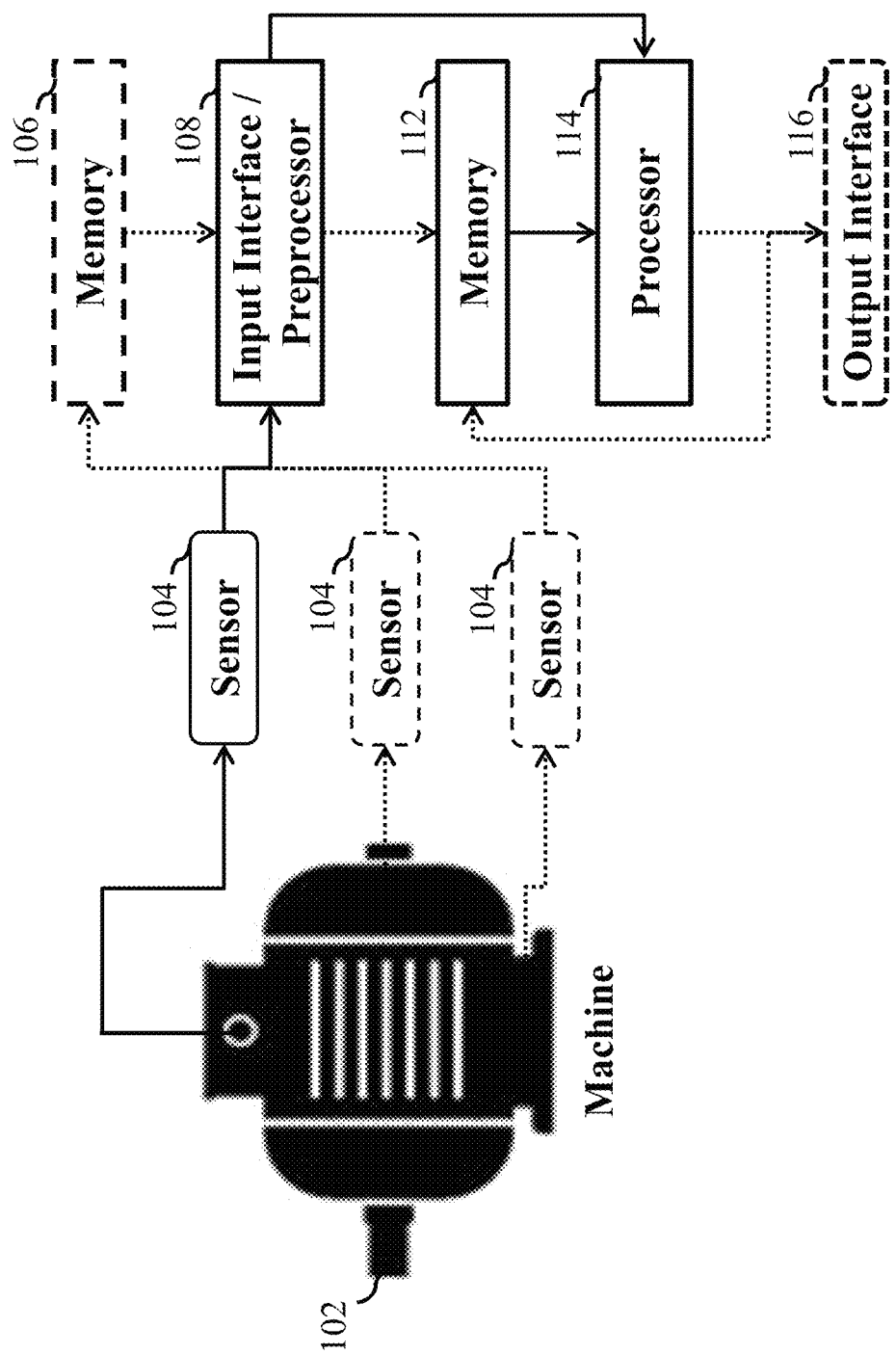
FIG. 1B is a block diagram illustrating components of the system of FIG. 1A, according to an embodiment of the present disclosure.

FIG. 1A and FIG. 1B are block diagrams illustrating system 100 for determining a pattern in time series data representing an operation of a machine 102, according to an embodiment of the present disclosure. The system 100 includes a sensor 104 in communication with the machine 102. A computer readable memory 112 to store and provide a set of time series data generated by the sensor 104 in communication with the machine 102. Wherein the times series data includes training time series data and test time series data, such that the time series data represents an operation of the machine 102 for a period of time, and the training times series data includes observations labeled with an outcome of the predictive inference. The sensor 104 collect operational data of the machine 102 that can be stored in memory 106 or directly to an input interface/preprocessor 108, and then sent to the processor 114. Upon being processed the data is either stored in memory 112 or outputted via the output interface 116.

Some embodiments of present disclosure are based on a realization that times series data generated from sensors 104 in communication with the machine 102, can be filtered using a set of recursive and stable filters at a training time, at a test time or both, to obtain a set of filtered time series data. Wherein, the training time uses the training time series data for the filtering and the test time uses the test time series data for the filtering. Such that each data point in the filtered time series data corresponds to an observation in the times series data that is a function of all previous observations. In other words, each data point carries information about potentially all past observations.

Still referring to FIG. 1A and FIG. 1B, the present disclosure relates to a problem of prediction and fault prognosis for physical systems, i.e. machines, whose state evolves according to a dynamical system and a stream of sensory observations in the form of a time series data that is made available from sensors in communication with the machines. At least one goal is to extract information from the time series data so that a machine learning algorithm/method can estimate a probability of a certain event(s) in the future, or an expected remaining useful lifetime of the physical system (machine). However, we found that trying to learn an estimator by directly using the history, is a significant challenge, because it is a time-varying vector with an ever increasing dimension. Some examples of dynamical systems that generate time series data are from the group consisting of one of: power generation turbines, aircraft and helicopter engines, internal combustion engines, various parts of a vehicle, rechargeable batteries, and elevators, etc.

Still referring to FIG. 1A and FIG. 1B, extracting a suitable state representation from time series data is at least one of the primary problems addressed by the present disclosure. For example, as noted above, we realized that by filtering time series data with a recursive and stable filters, each data point in the filtered time series data corresponds to an observation in the times series data is a function of all previous observations. In such a manner, each data point carries information about potentially all past observations. To put it another way, we discovered how to obtain more information about the actual state of the machine, in order for the machine learning methods to be used to design the various predictors, i.e. predictive inferences. The predictive inference can be from the group consisting of one of: a time series prediction; an estimate of remaining useful lifetime for the purpose of fault prognosis; fault recognition and detection; fault diagnosis; or other machine learning tasks that benefit from a summary of the time series data.

The recursive filter may include a software module with internal states stored in memory, and receives the time series data as an input, then outputs a value based on the internal state of the software module and the received input, and updates the memory. The stable filter may include a rational polynomial, wherein a denominator of the rational polynomial is a polynomial with roots that are either real or complex, such that a magnitude of the roots is equal to or smaller than one.

Moreover, through experimentation we learned that the training data can be filtered with a set of filters including multiple random filters to produce a set of filtered data. The data points from different filtered data that correspond to the same observation have the same label and can form the informational vector used in the machine learning methods. Wherein a number of filters defines a size of the informational vector.

Based upon our realization, we determine the model for the predictive inference on the operation of the system/machine, by using a number of filters to provide an approximate state of the system/machine. If the number of filters are increased, then so also the quality of the approximation or prediction.

For example, a number of filters selected from the set of filters may be selected based on hardware limitations of the non-transitory computer storage medium and hardware limitations of the processor, and in combination with a model selection procedure that is based on a quality of the prediction of the predictive inference model. Further, a number of filters in the set of filter can be dependent upon a function of a maximum number of filters capable of being processed based on a hardware capacity of the non-transitory computer storage medium and hardware processing limitations of the processor, and an exact number of filters required for optimizing a quality of the prediction of the model of the predictive inference that is based on the model selection.

It is possible that for each filter in the set of filters can be processed in parallel with other filters in the set of filters by the processor that are stored in memory.

Still referring to FIG. 1A and FIG. 1B, regarding the type of filters in the set of filters, the set of filters can be random projection filters that collectively define a Random Projection Filter Bank (RPFB). The RPFB can include a set of autoregressive filters with randomly chosen parameters that act on the input which is in a form of a time series data and an output of an information vector. Further still, the time series can be processed by each filter in the set of filters in the RPFB, and generate an output from each filter, such that the output of each filter is a time series. The processor may determine the set of filters by randomly choosing a set of numbers that define a set of randomly selected stable and recursive filters, such that the recursive filters include auto regressive filters and non-auto regressive filters, and the stable filters include non-divergent filters. If additional time series data is accessed, the output time series can also change.

Further, the RPFB can process the time series data and provide a vector that approximately summarizes the time series data, wherein an output of the RPFB describes a low-dimensional dynamical system having a dimension smaller than a dimension of the vector describing the time series. The RPFB can be a method to approximately summarize a time series generated by an unknown dynamical system/machine. Wherein the RPFB can provide an approximate sufficient statistic of the history. For example, the RPFB projects the sequence of observations $X_1, X_2, \ldots, X_t$ to a low-dimensional dynamical systems, with a constant dimension $d \leq t$ for any $t=1, 2, \ldots$. The dimension d can be selected to be much smaller than the size of the time series data. An aspect of RPFB can be based on randomly generating many simple dynamical systems, i.e., filters. Wherein we then can approximate the true dynamical system as a linear or nonlinear combination of this randomly generated set of filters.

Further, the RPFB can include a multitude of stable random projection filters, wherein each random projection filter is a stable autoregressive-moving average filter that is described by numerator and denominator polynomials with randomly chosen poles and zeros, wherein the poles are roots of the denominator's polynomial and the zeros are roots of the numerator's polynomial.

After we have determined the model for the predictive inference on the operation of the system/machine, the determined model can be stored in memory or outputted via an output interface. Wherein, the output of the determined model for the predictive inference can be the input of another machine learning module that predicts the next state of the system/machine, or the type of fault, or remaining useful life. At least one advantage in the rapidly increasing volume of data collected from industrial equipment is that the systems and methods of the present disclosure make it possible to continuously assess remotely the health of such equipment, correctly diagnose faults when they occur, and even estimating when they would occur in the future. Such fault diagnosis and prognosis capability can enable optimal allocation of spare parts, repair crews, and also minimize equipment downtime and repair costs, according to the present disclosure.

Figure 1C:
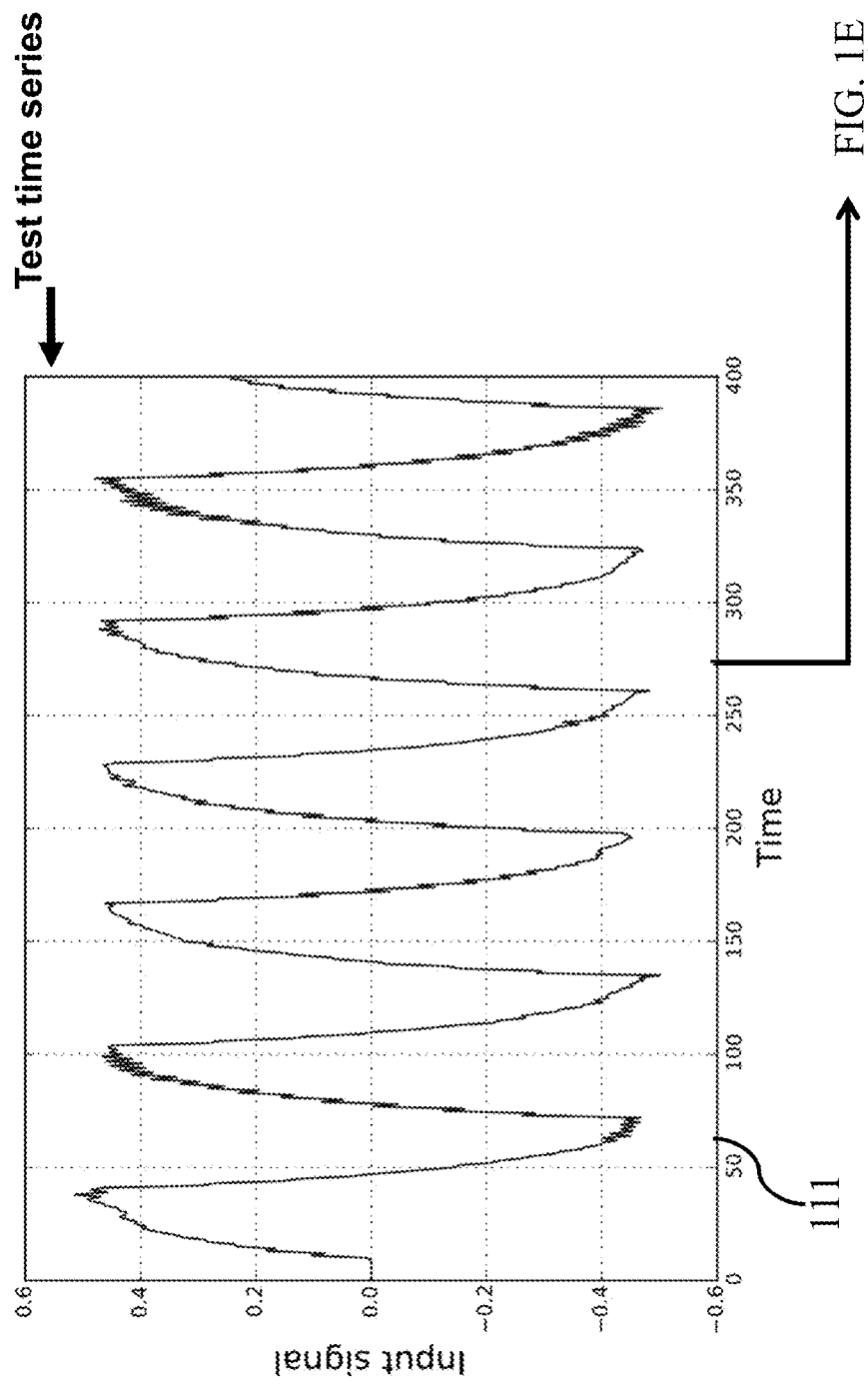
FIG. 1C and FIG. 1D are graphs and FIG. 1E is a block diagram, illustrating the main modules of a predictive inference algorithm in FIG. 1A, according to an embodiment of the present disclosure.
Figure 1D:
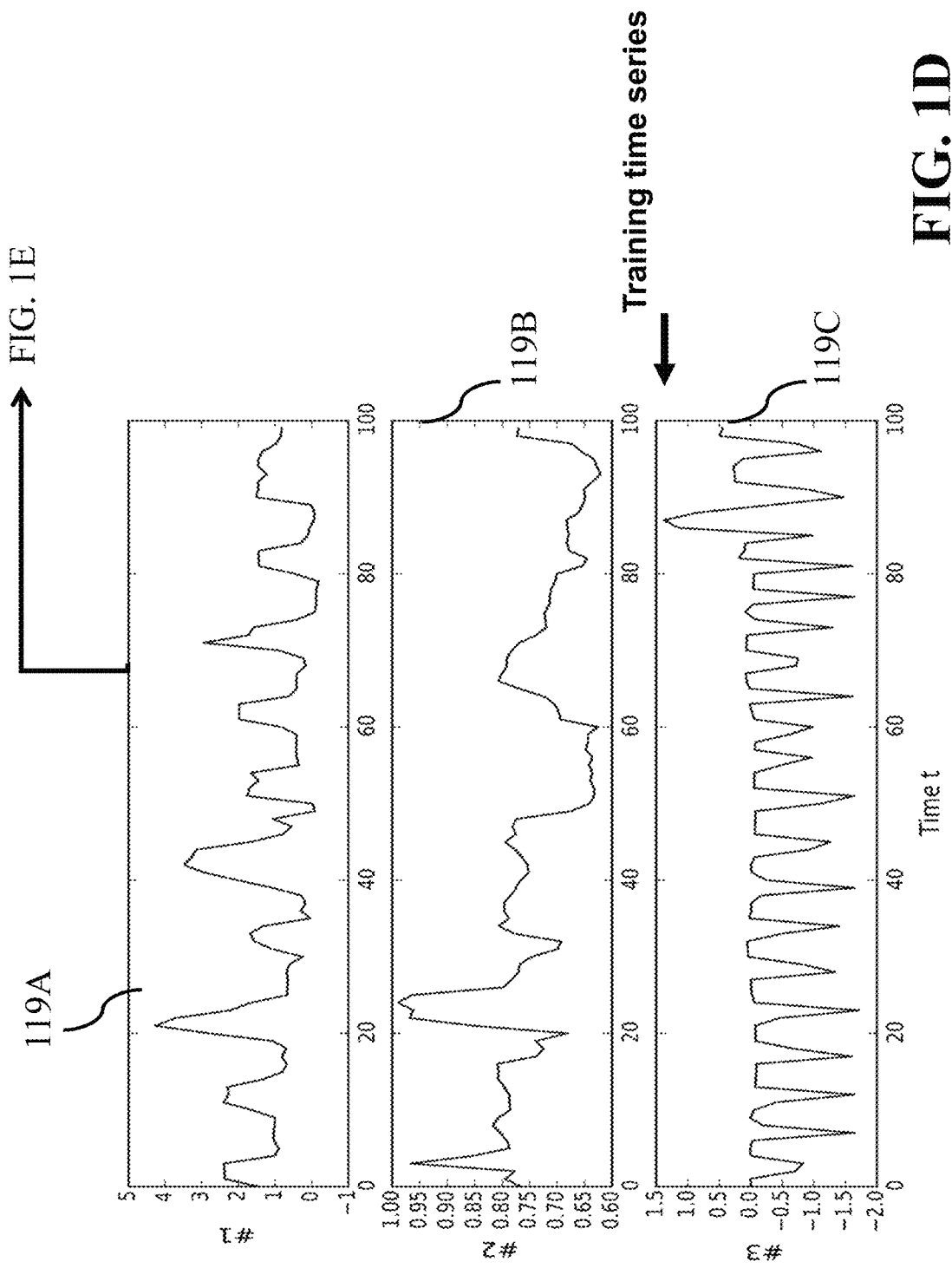
Figure 1E:
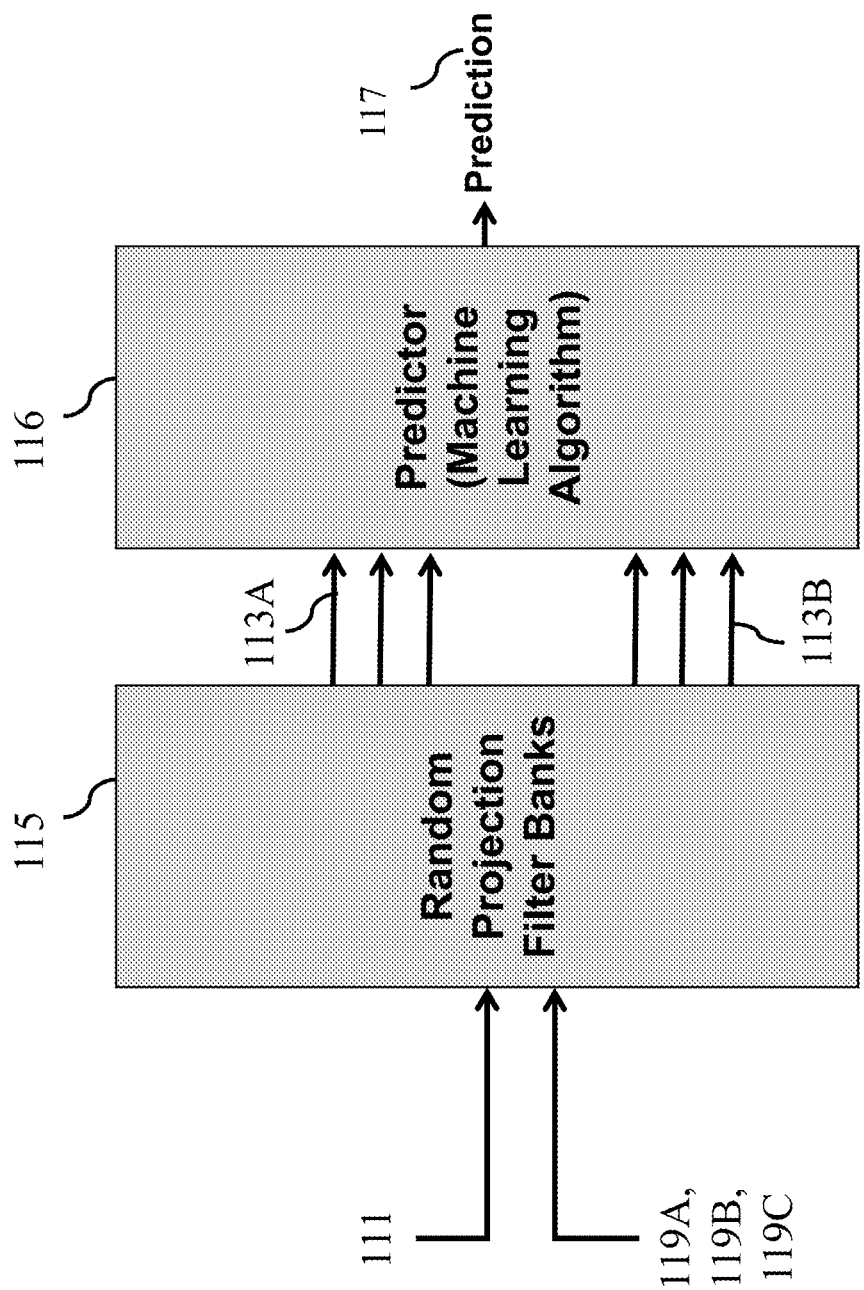

FIG. 1C and FIG. 1D are graphs and FIG. 1E is a block diagram, illustrating how the predictive inference model is determined based on the training and testing time series data, the RPFB, and the predictor. The training time series 119A, 119B, 119C of FIG. 1D is collected previously, whereas the test time series 111 of FIG. 1C is received from the sensors of the machine. Both time series go through the RPFB, in which each time series passes through the set of randomly generated stable recursive filters. The output is a time series of informational vector 113A, 113B of FIG. 1E has a dimension d equal to the number of filters in the RPFB. This informational vector is given as input to a predictor, which is a machine learning algorithm. The choice of predictor depends on the problem that is solved. If the goal is to estimate the Remaining Useful Lifetime of the machine, this can be any standard regression estimator that can work with multi-dimensional input. For the fault diagnosis, this can be a classifer. The output 117 of FIG. 1E is the prediction of the predictive inference model.

To better provide an understanding of how the embodiments of the present disclosure may be completed, at least one embodiment includes a system that initially starts (i.e. Step 1 of FIG. 1A) by accessing a set of time series data. Wherein the time series data generated by sensors in communication with a machine and stored in memory. It is possible the time series data is acquired via an input interface in communication with a processor. For example, a user interface in communication with the processor and the memory, acquires and stores the time series data in the memory upon receiving an input from a surface of the user interface by a user, so the time series data is capable of being accessed by the processor. Further, the time series data includes training time series data and test time series data, wherein the time series data represents an operation of the machine for a period of time, and the training times series data includes observations labeled with an outcome of the predictive inference.

Step 2 of FIG. 1A includes applying a set of recursive and stable filters for filtering at a training time, at a test time or both, to the times series data to obtain a set of filtered time series data, such that a data point in the set of filtered time series data corresponds to an observation in the time series data that is a function of the corresponding observation and past observations in the time series data preceding the corresponding observation. Remember, we realized that by filtering time series data with a recursive and stable filters, each data point in the filtered time series data corresponds to an observation in the time series data is a function of all previous observations. Which means, each data point carries information about potentially all past observations. More specifically, we are able to obtain more information about the actual state of the machine, in order for the machine learning methods to be able used to design the various predictors, i.e. predictive inferences, based on our realization.

The training includes a collection of time series data obtained at a previous time. This can be obtained by the designer of the predictive inference machine and stored memory device 106, or it can be gradually collected while the machine is operating. The whole or a part of training time series data is first passed through the RPFB, whose output is a time series of informational vector. The informational vector provides the input for a machine learning algorithm. The machine learning algorithm can be a classifier, a regression estimator, or a survival analysis estimator, or any other standard machine learning method. The choice is determined by the problem that should be solved. The machine learning algorithm processes the informational vector produced by the training time series and provide a predictive model, which can then be stored in a memory 112.

The testing includes the time series that is obtained from sensors of a machine 102, and the predictive inference is supposed to be applied to it. The test time series data go through the same RPFB to provide an informational vector. The vector is then given to the predictive model provided by the machine learning algorithm. The predictive model provides an output which can be an estimate of the Remaining Useful Life of a machine or the determination of whether the machine is faulty or not, or any other predictive task.

Step 3 of FIG. 1A, includes determining the model for the predictive inference using the training time series data, based on filtering the training time series data with a set of filters to produce a set of filtered training time series data, so as to obtain the determined model for the predictive inference. As noted above, through experimentation we learned that the training data can be filtered with multiple random filters to produce a set of filtered data. The data points from different filtered data that correspond to the same observation have the same label and can form the informational vector used in the machine learning methods. Wherein a number of filters defines a size of the informational vector.

Finally, step 4 of FIG. 1A, explains that the determined model for the predictive inference can either be stored in memory, or outputted via an output interface in communication with the processor, to be an input of another machine learning method/module that predicts a next state of the machine, or a type of fault, or a remaining useful life.

Aspects of Components of the Present Disclosure

Referring to FIG. 1B, the components may provide for additional features of the present disclosure. For example, the processor 114 may be part of a computer 110, i.e. computer or processor, wherein the computer 110 can include an input interface 108 to receive the time series data from the sensor 104 and/or receive the time series data from possibly an external memory device 106. Wherein the external memory device 106 stores the time series data generated by the sensor 104 from the operation of the machine 102. However, it is possible that the system is based on real-time, such that the sensor 104 may be directly in communication with one of the input interface 108, memory 112 or processor 114, depending upon the specific needs of the system, user of the system, requiring a specific operational configuration of the system. Further, the sensor 104 may generate data that includes parameters, such that each parameter can relate to the operation of the machine including one or a combination of: fluid force data, fluid energy data, vibration data, temperature data, voltage data or current data.

Still referring to FIG. 1B, the sensors 104 may continually measure electrical properties of the machine and provide streams of sensor data, which may be stored and/or processed onsite or relayed to another location. The sensors 104 can measure/sense a parameter such as pressure of machine or other measurable like parameters. For example, the sensors 104 may sample the parameters from the machine 102 at an interval of once per day during one week and at a different interval during another week. Further, timing information identifying the entry time, date and time, of the training data stream into the memory 112 can be included in the memory 112. Also, timing information for use in identifying invalid data in the training data streams may be stored in the memory 112. For example, invalid data may be a result of a failed sensor.

Still referring to FIG. 1B, it is contemplated the individual machines may be from the group consisting of elevators, cars, air conditioners, electrical motors, generators, etc., and even entire factories. Further, it is possible the time series data is data gathered from an organ of an animal, such as a human, that provides an electrical pattern that may be monitored or recorded via the sensor 104, so data may be obtained and processed by the system 100 of the present disclosure.

Still referring to FIG. 1B, the input interface/preprocessor 108 can be configured to detect failed sensors upon receiving data from the sensor, wherein if the sensor is determined to be failed, any data associated with the failed sensor during a specific time period may be removed. It is possible the input interface/preprocessor 108 may extract the time series data only from portions of the time series data stream that do not include invalid data (invalid data referring to, for example, time series data generated while the sensor was malfunctioning) based on information, i.e. timing or other information, that is provided along with the time series data. The input interface/preprocessor 108 may also consider time series data stored in the memory 112 for a long time, over a pre-specified by a user of a period of time, day(s), etc., after generation of the time series data stream by the sensor 104 as invalid and exclude portions of the time series data stream that include such data. The interface/preprocessor 108 may perform the extraction of the time series data, wherein the time series data includes segments of time series data. Such that an overlap between adjacent time series data segments is adequate to reduce unwanted redundancy of the data between the adjacent time series data segments. It is noted, the overlap between adjacent time series data can be set or limited to a maximum of about 10%, 30%, 40%, 50%, 60%, 70% or 80%, or some increment between 10% and 80%, such as 15%, 25%, 35%, etc.

An Embodiment of the Steps of the Present Disclosure

Figure 1F:
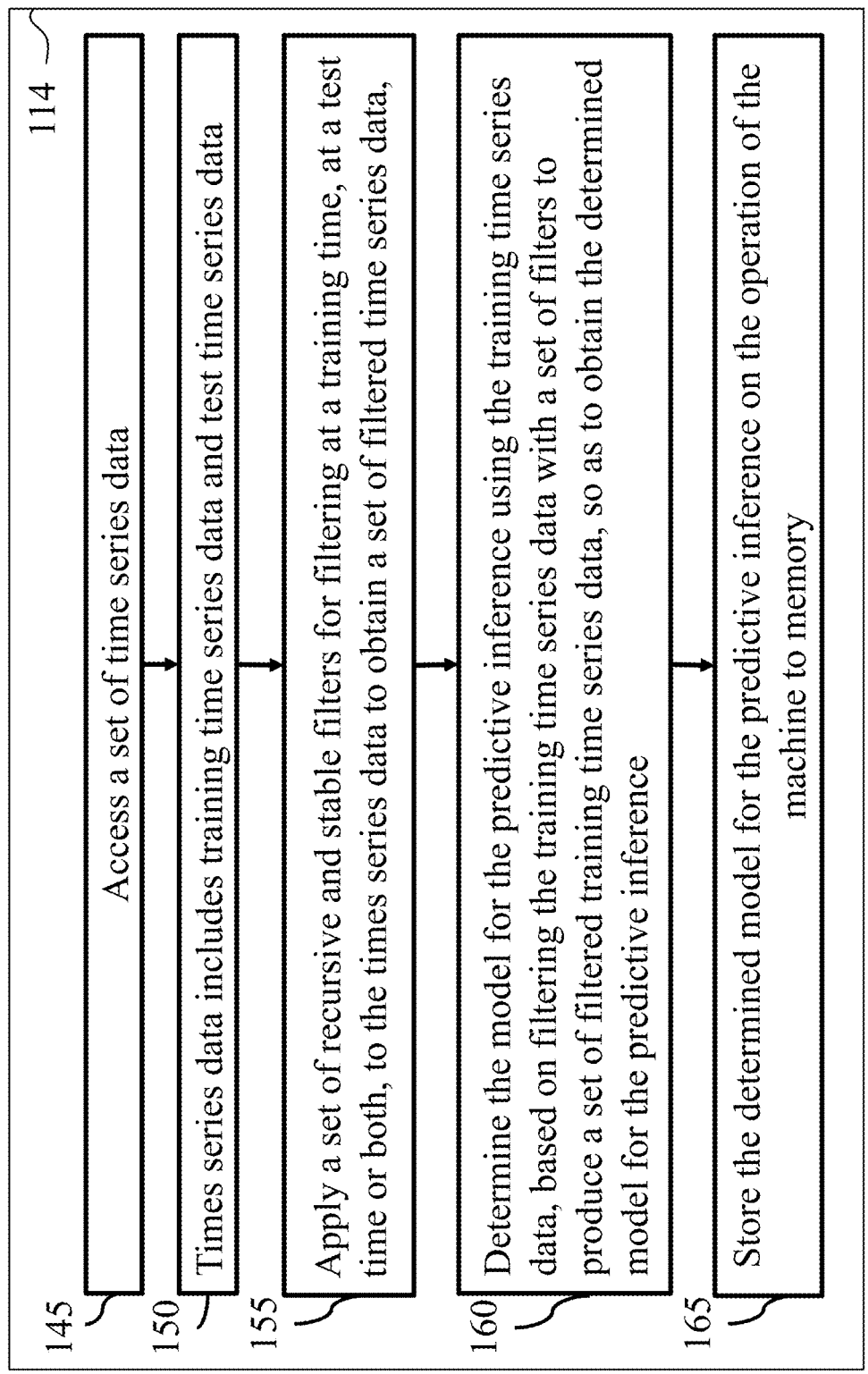
FIG. 1F is a block diagram illustrating the system steps of FIG. 1A, for determining the model for a predictive inference on the operation of the machine, according to an embodiment of the present disclosure.

FIG. 1F is a block diagram illustrating the system steps of FIG. 1A, for determining the model for a predictive inference on the operation of the machine, according to an embodiment of the present disclosure.

Referring to steps 145 and 150 of FIG. 1F, step 145 includes accessing the memory 112 to acquire the set of time series data. Step 150 defines that the times series data having training time series data and test time series data, wherein the time series data represents an operation of the machine for a period of time, and the training times series data includes observations labeled with an outcome of the predictive inference.

Step 155 of FIG. 1F includes applying a set of recursive and stable filters for filtering at a training time, at a test time or both, to the times series data to obtain a set of filtered time series data, such that a data point in the set of filtered time series data corresponds to an observation in the time series data that is a function of the corresponding observation and past observations in the time series data preceding the corresponding observation.

Step 160 of FIG. 1F includes determining the model for the predictive inference using the training time series data, based on filtering the training time series data with a set of filters to produce a set of filtered training time series data, so as to obtain the determined model for the predictive inference.

Finally, step 165 of FIG. 1F includes storing the determined model for the predictive inference on the operation of the machine to memory or outputting the determined model via the output interface in communication with the processor.

Figure 2:
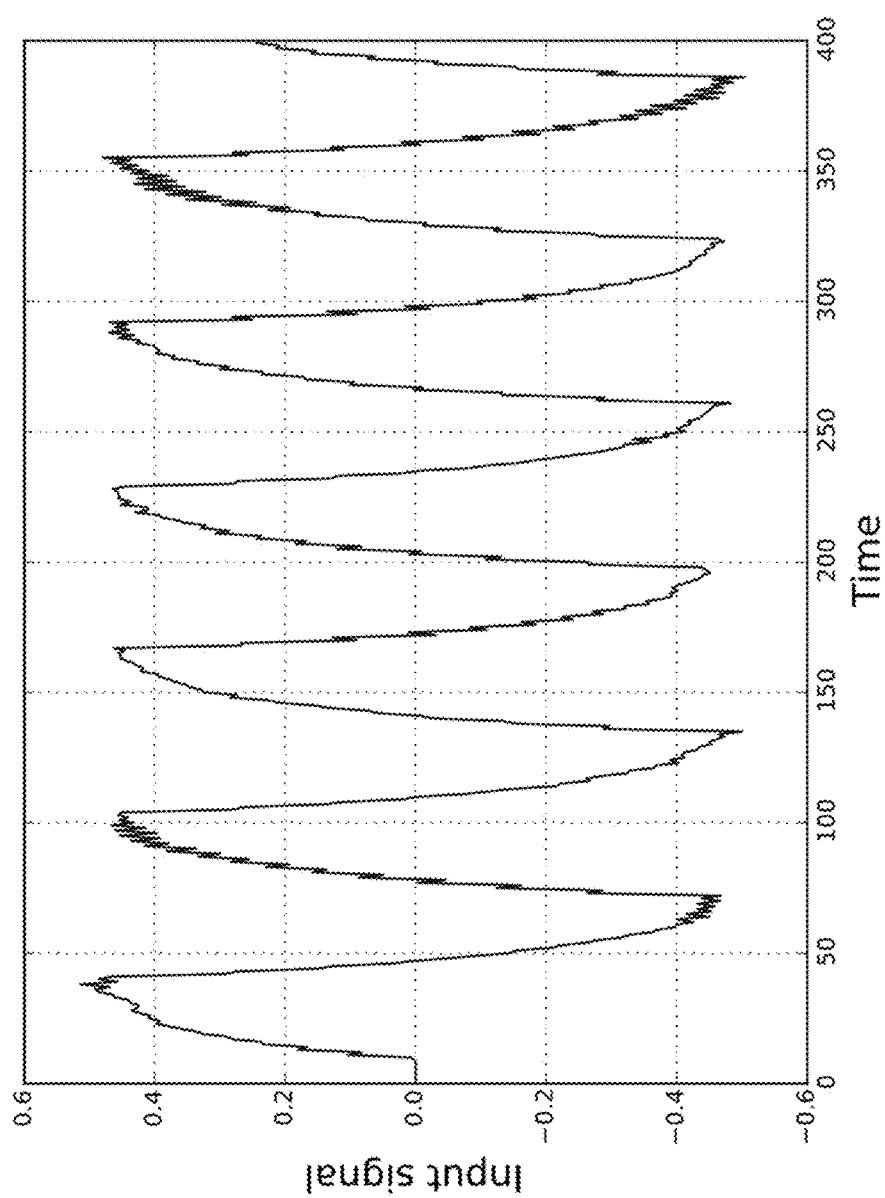
FIG. 2 is a graph illustrating a sample input time series, according to an embodiment of the present disclosure.

FIG. 2 is a graph illustrating a sample input time series data, according to an embodiment of the present disclosure. This time series data can be either the training time series data or the test time series data, and it only serves to show some steps of the algorithm. The input time series can be written as $X_1, X_2, X_3, \ldots$ in which each $X_t$ is a real-valued number or a real-valued vector.

Figure 3:
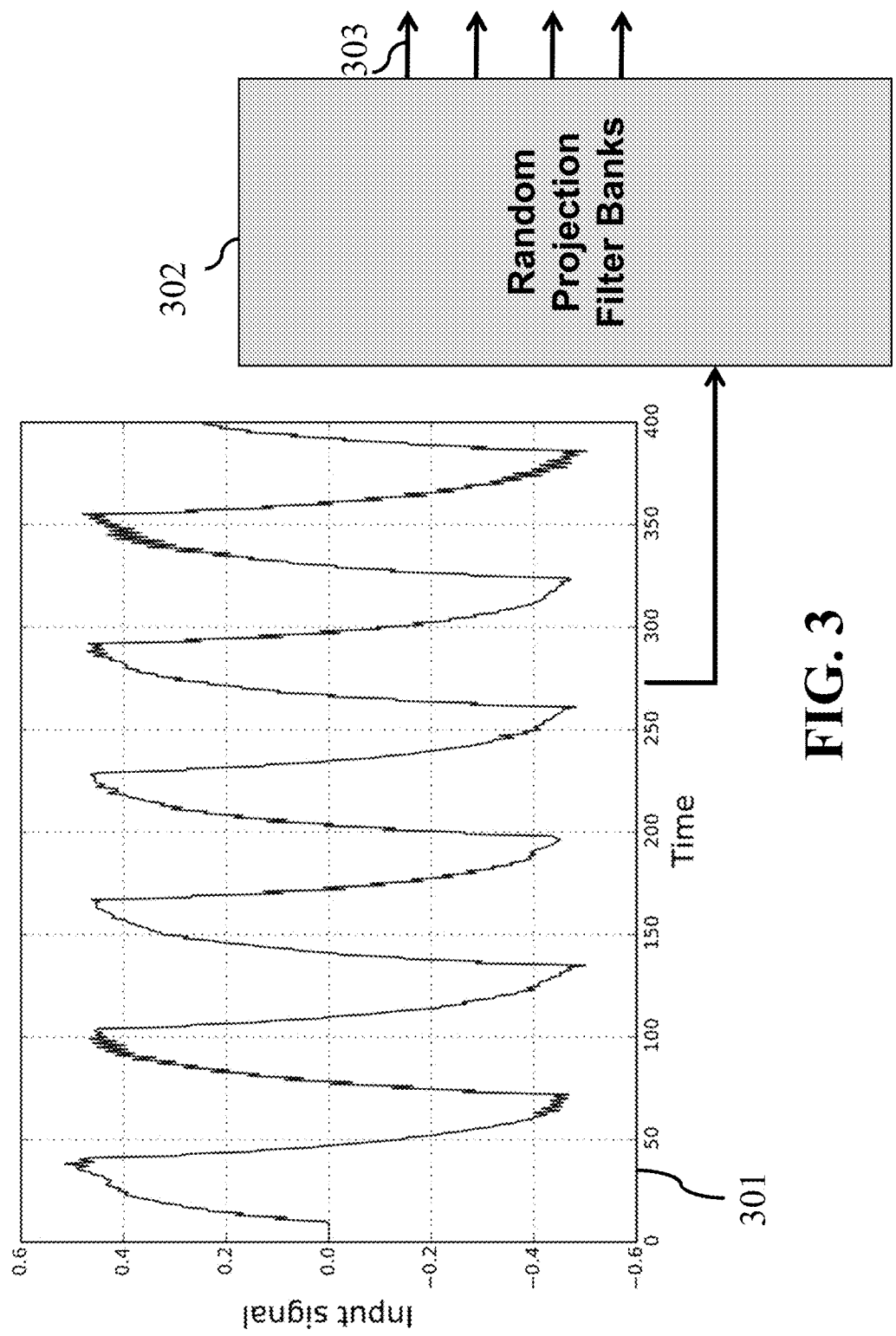
FIG. 3 is a graph illustrating a sample input time series being processed by random projection filter bank, according to embodiments of the present disclosure.

FIG. 3 is a graph illustrating the input time series 301 going through the RPFB, according to embodiments of the present disclosure. The input time series $X_1, X_2, X_3, \ldots$ is going through the RPFB 302 and generates a multitude of time series as output 303. The number of generated output time series is the same as the number of filters d in the RPFB. The RPFB 302 is the same as 115 in FIG. 1E. The input time series 301 can be either the training time series 119A, 119B, 119C of FIG. 1D or the test time series 111 in FIG. 1C.

Figure 4A:
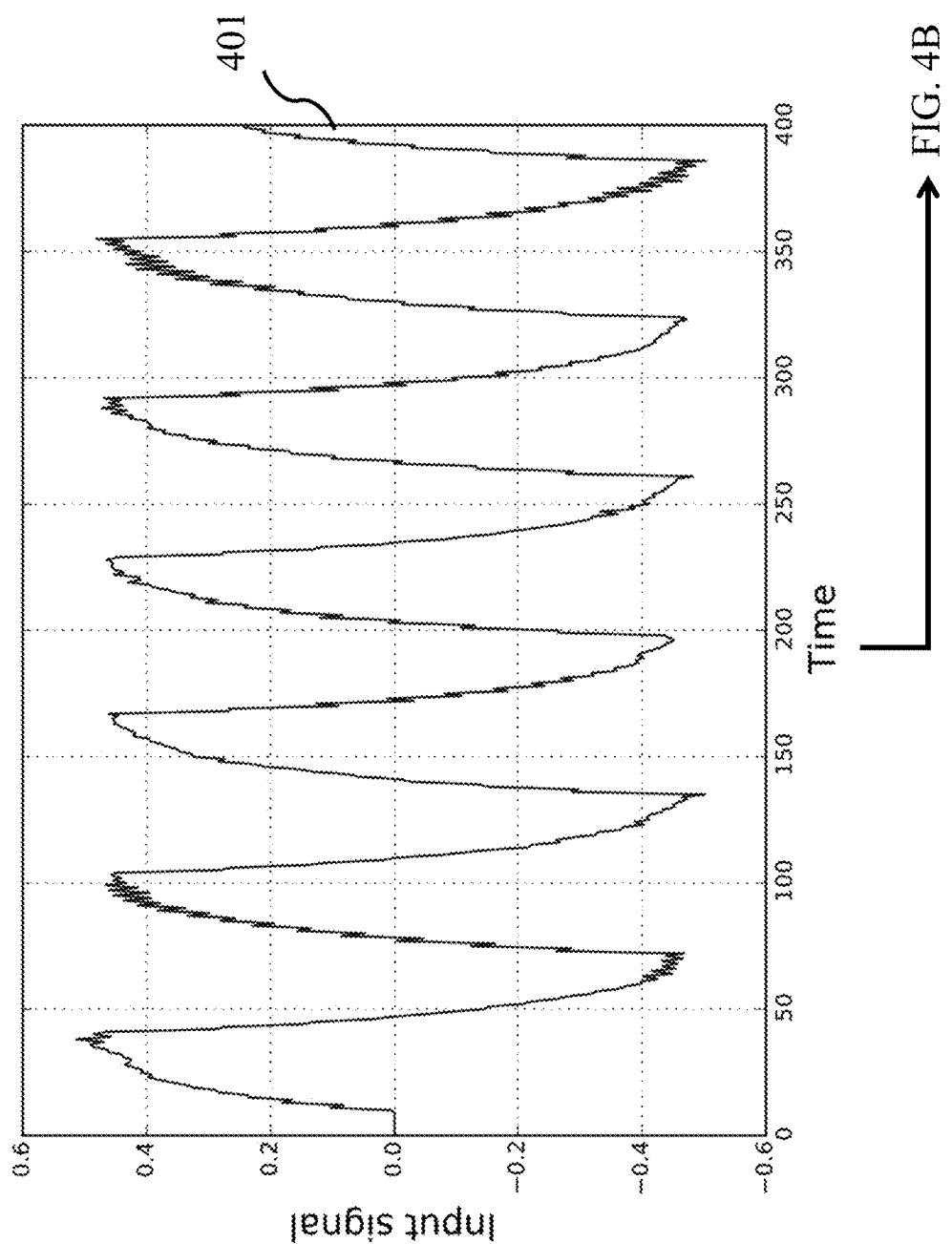
FIG. 4A and FIG. 4B are graphs illustrating the impulse response of a few of random filters in the random projection filter bank, according to embodiments of the present disclosure.
Figure 4B:
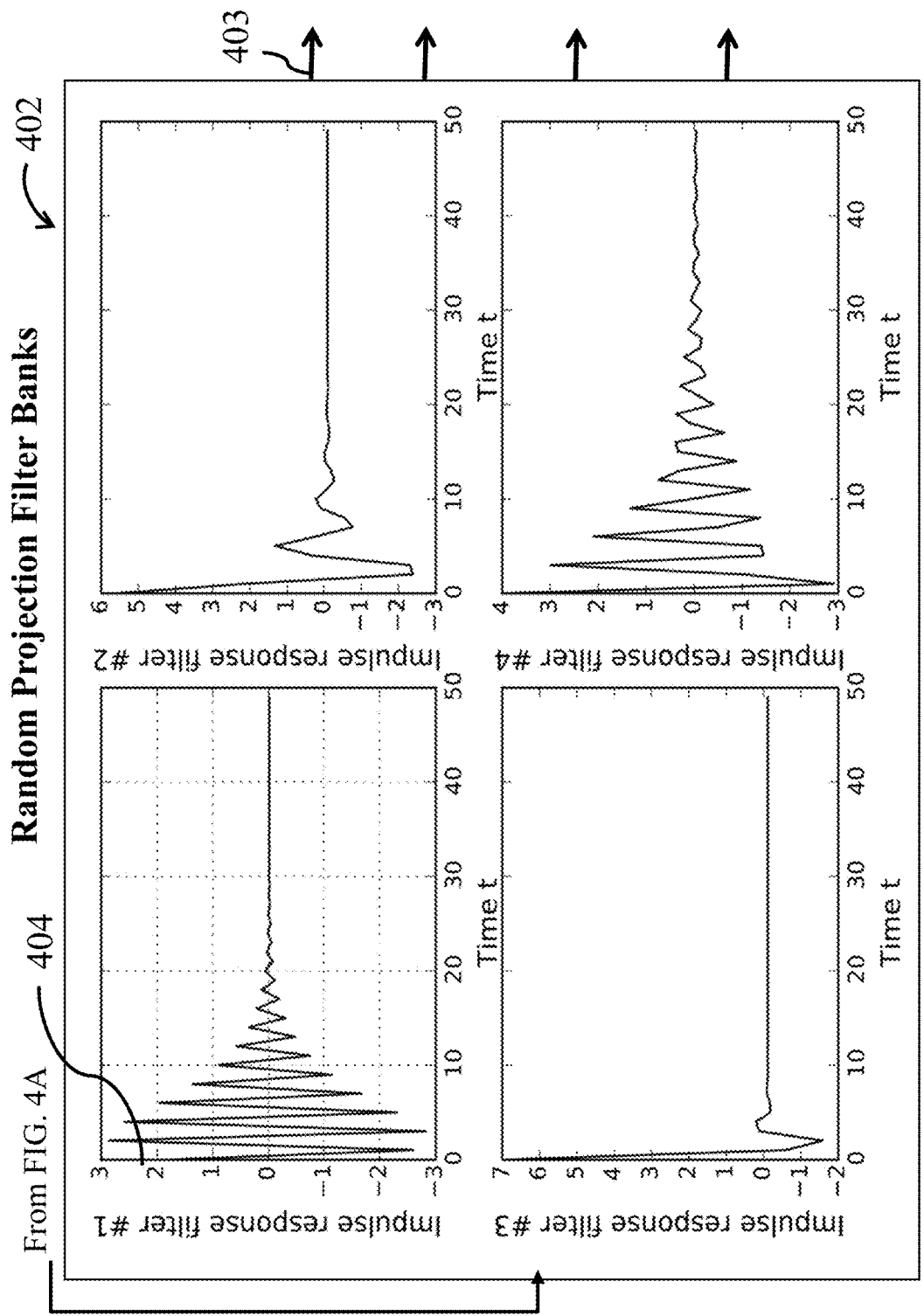

FIG. 4A and FIG. 4B are graphs illustrating the internal working of a RPFB, according to embodiments of the present disclosure. There are d random projection filters 402 inside the RPFB. Each filter is a randomly generated recursive and stable filter that takes a time series as its input and generates a time series as its output. The combination of the outputs of all d filters generates the informational vector output of the RPFB.

Referring to FIG. 4A and FIG. 4B, FIG. 4A illustrates the input 401 is the same as 301 in FIG. 3, and the output 403 is the same as 303 in FIG. 3. FIG. 4B illustrates the impulse responses of random projection filters inside the RPFB as shown in 404. There can have a variety of different behaviors, some of with more or less oscillation and different times to decay. These behaviors are randomly generated. To define mathematically, we can use the language of Z-transforms. We have $z^{-1}$ as the time-delay operator such that $z^{-1}X_t = X_{t-1}$. With this definition, the rational polynomial $$\phi(z^{-1}) = \frac{1}{1 - Z'z^{-1}}$$

defines a autoregressive filter with a pole at Z'. This is a recursive filter. If Z', which can be a complex value, has a magnitude smaller than 1, this defines a stable filter. If we generate d random $Z_i'$ (i=1, ..., d), the vector of filters $$\phi(z^{-1}) = \left( \frac{1}{1 - Z_1'z^{-1}}, \frac{1}{1 - Z_2'z^{-1}}, \cdots, \frac{1}{1 - Z_d'z^{-1}} \right),$$

defines the RPFB. This set of filters should be stored in a memory and is used for processing both the training time series and the test time series.

Figure 5B:
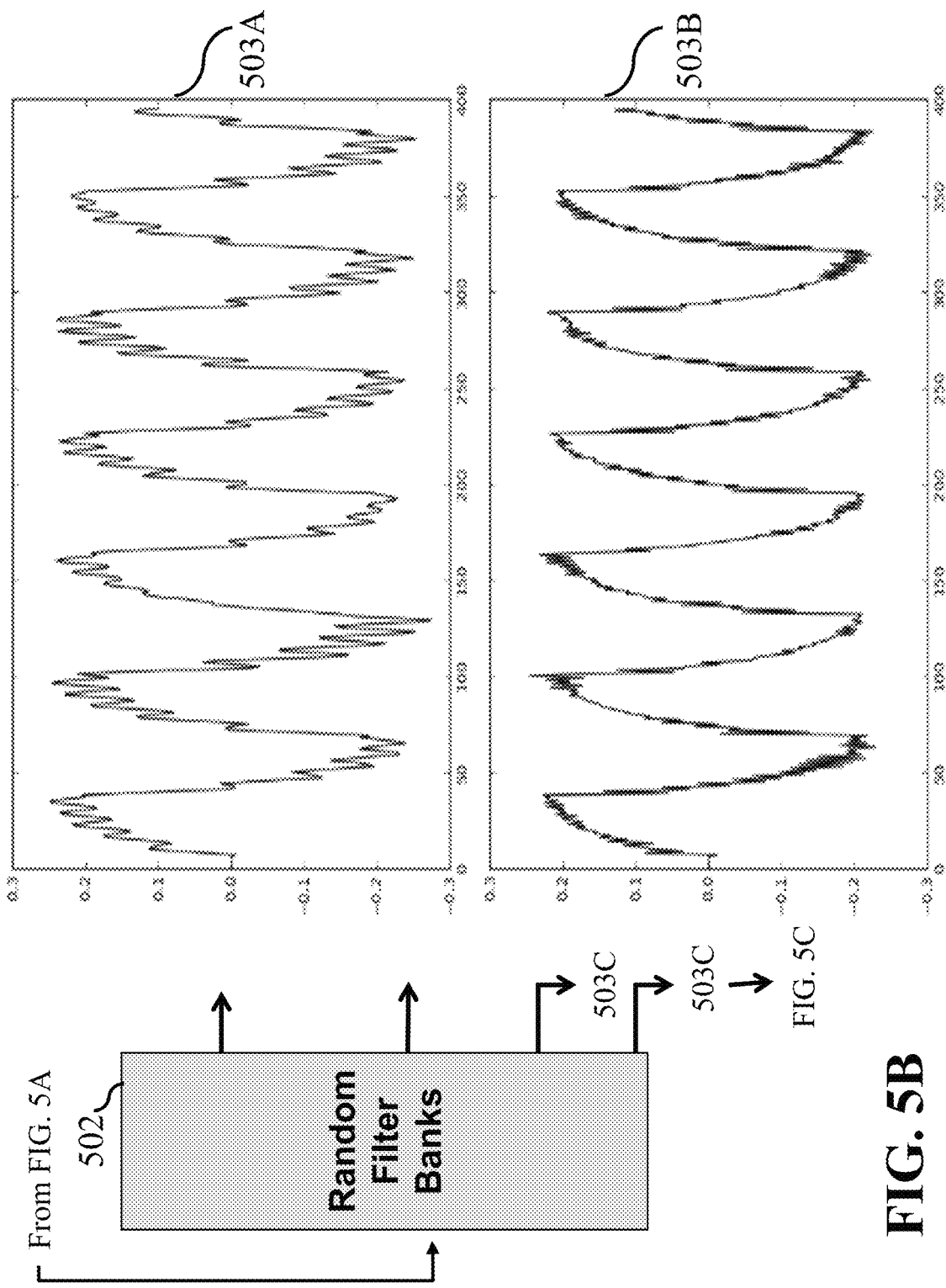
Figure 5C:
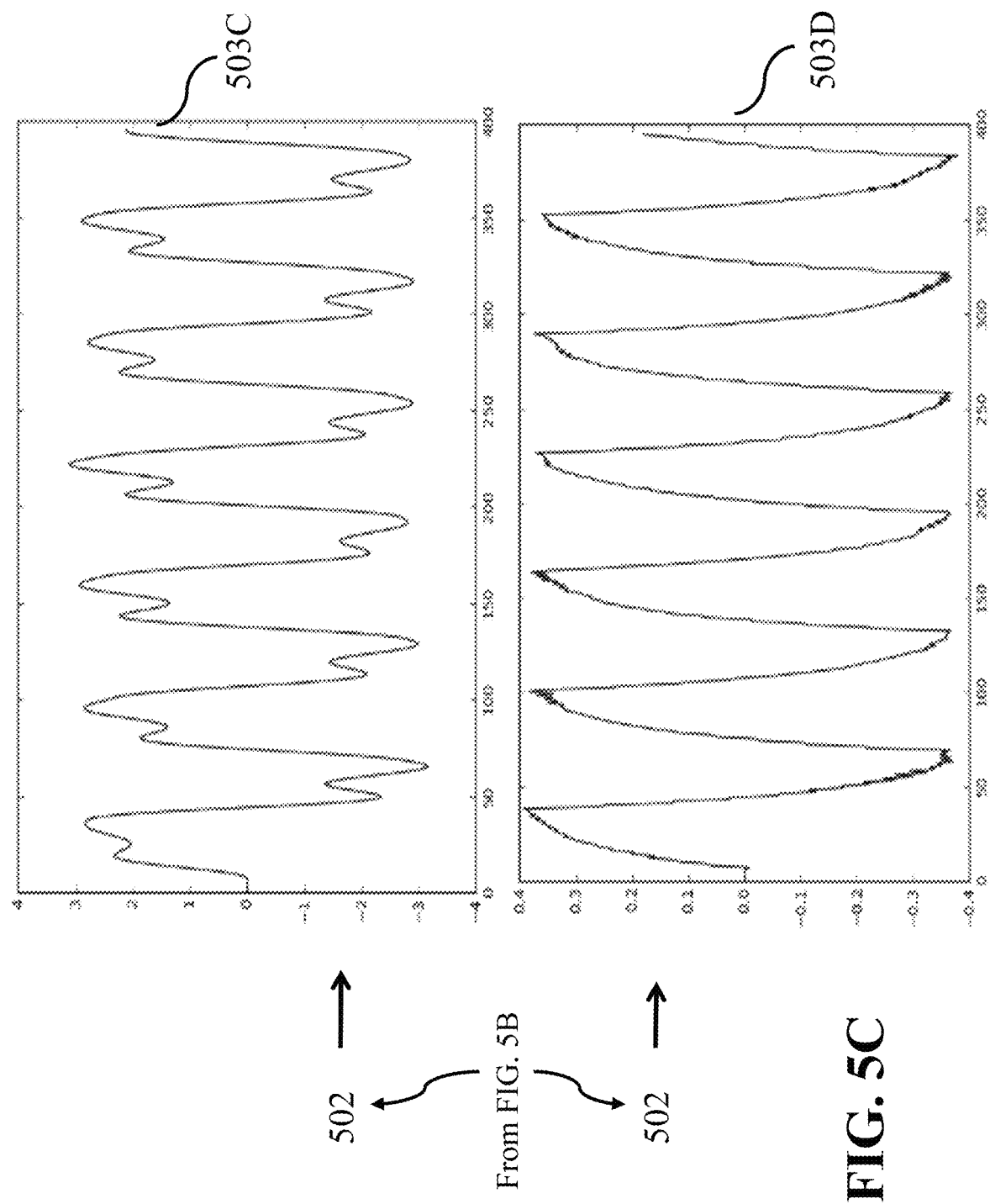

FIG. 5A, FIG. 5B and FIG. 5C are graphs illustrating the sample output of the RPFB given an input time series, according to embodiments of the present disclosure. FIG. 5A is a sample input time series 501 goes through the RPFB 502 of FIG. 5B and generates a multitude of output time series 503A and 503B of FIG. 5B, 503C and 503D of FIG. 5C. The vector corresponding to each time step of the output time series define an informational vector, which is given to the Predictor 116. Depending on whether the input time series is the training time series 119A, 119B, 119C or the test time series 111, the informational vector defined based on 503A, 503B, 503C, 503D corresponds to 113A or 113B, respectively.

Figure 6:
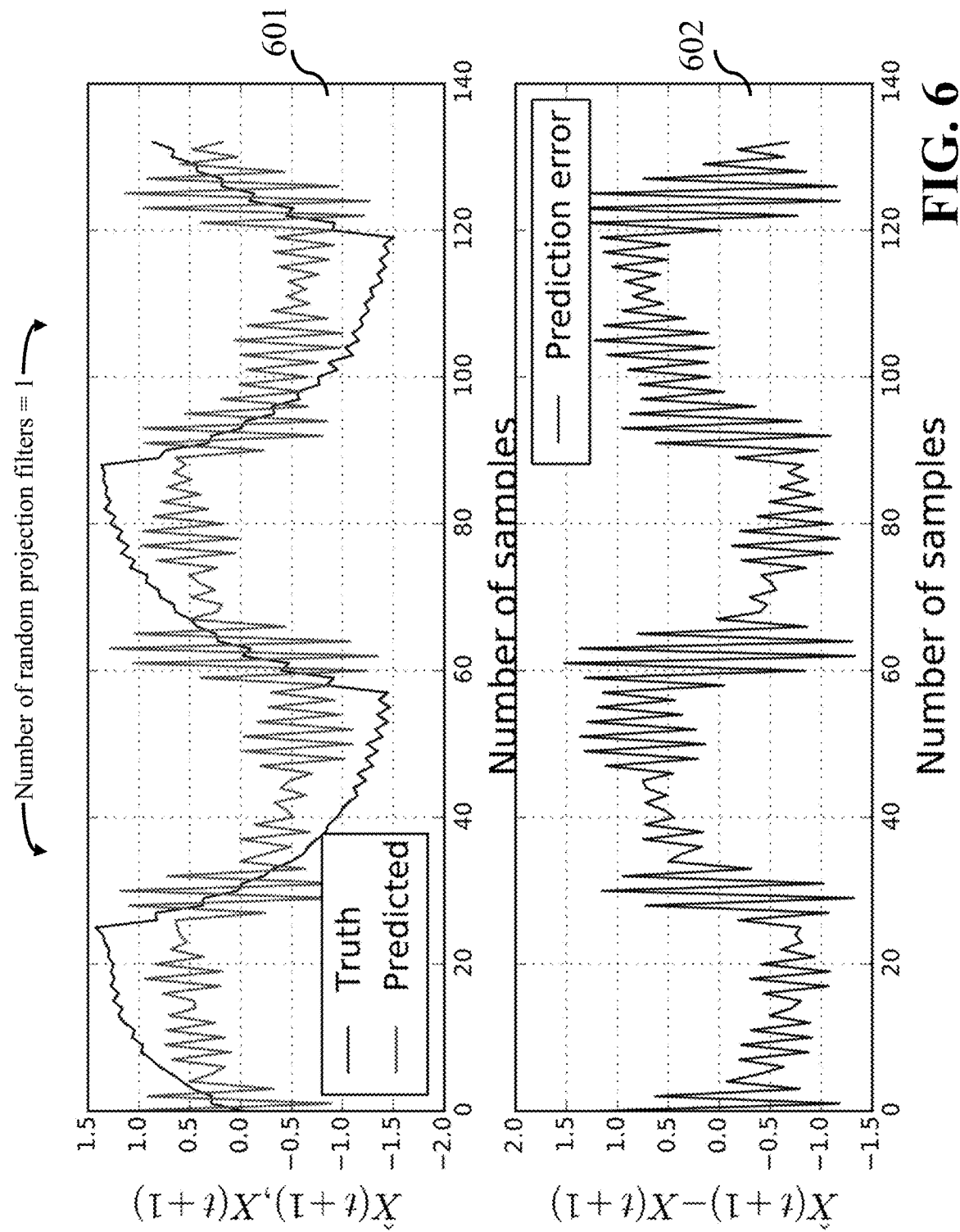
FIG. 6 is a graph illustrating a sample performance of a predictive inference for time series prediction using one (1) random projection filter within random projection filter bank, according to embodiments of the present disclosure.

FIG. 6 is a graph illustrating an example of predictive inference, according to embodiments of the present disclosure. Here the number of random projection filters is d=1 and the predictive inference task is to predict the next time step $X_{t+1}$ based only on the time series $X_1, \ldots, X_t$. The true time series and the predicted time series is shown is 601. The error between them is shown is 602.

Figure 7:
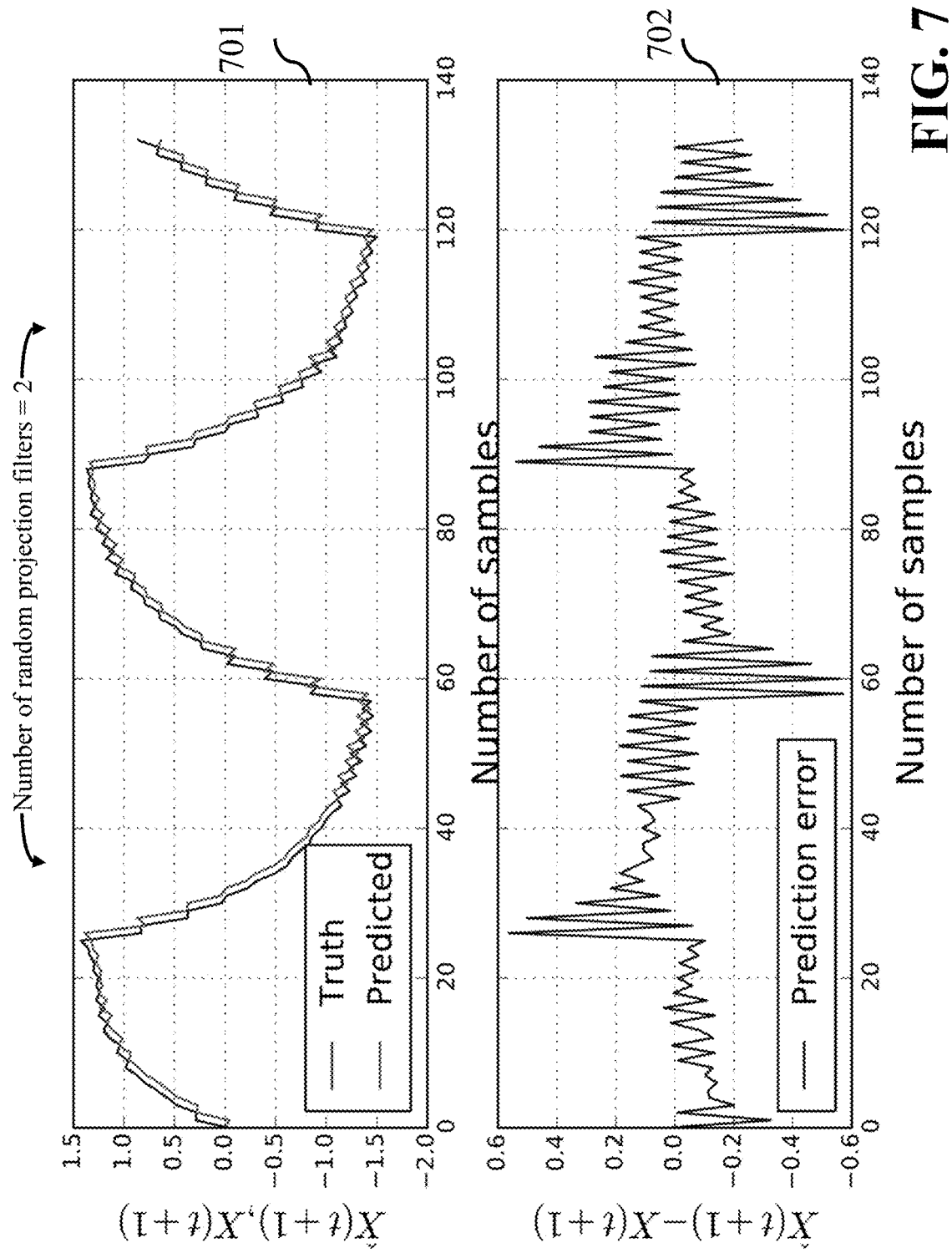
FIG. 7 is a graph illustrating a sample performance of a predictive inference for time series prediction using two (2) random projection filters within random projection filter bank, according to embodiments of the present disclosure.

FIG. 7 is a graph illustrating an example of predictive inference, according to embodiments of the present disclosure. Here the number of random projection filters is d=2. The true time series and the predicted time series is shown is 701. The error between them is shown is 702. The error is smaller in 702 compared to 602.

Figure 8:
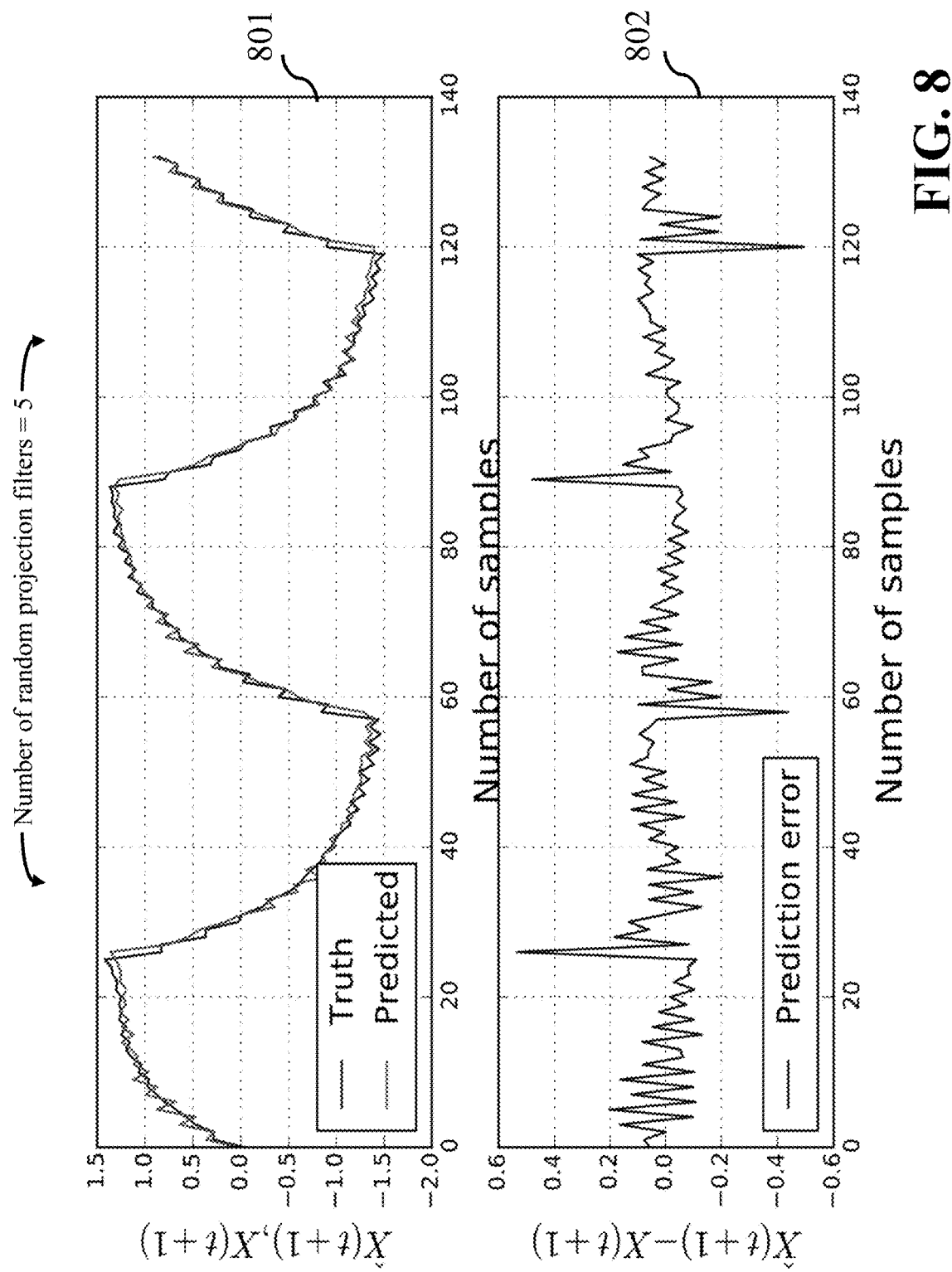
FIG. 8 is a graph illustrating a sample performance of a predictive inference for time series prediction using 5 random projection filter within random projection filter bank, according to embodiments of the present disclosure.

FIG. 8 is a graph illustrating an example of predictive inference, according to embodiments of the present disclosure. Here the number of random projection filters is d=5. The true time series and the predicted time series is shown is 801. The error between them is shown is 802. The error is smaller in 802 compared to 702 and 602.

Figure 9:
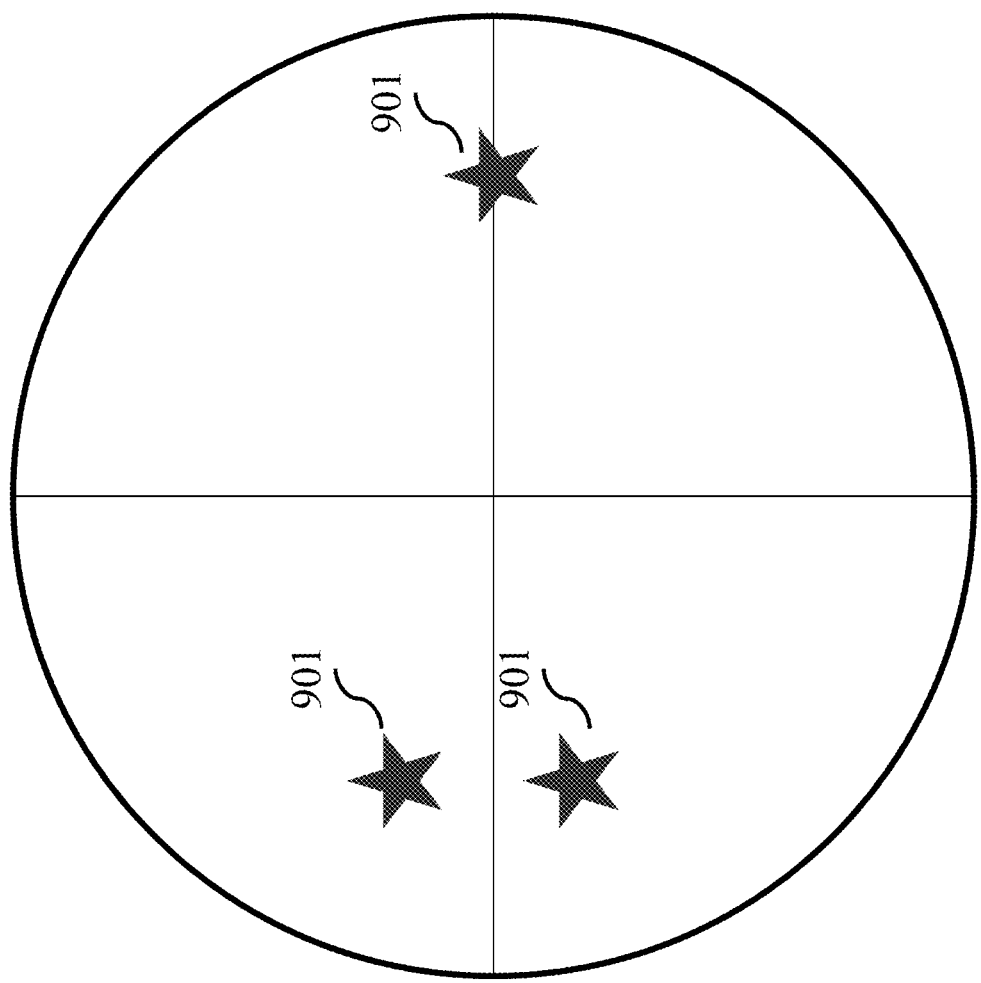
FIG. 9 is a graph illustrating an example of location of poles of an autoregressive-moving average filter with a pair of conjugate roots and a simple root, according to embodiments of the present disclosure.

FIG. 9 is a graph illustrating an example of location of poles 901 of an unknown autoregressive-moving average filter with a pair of conjugate roots and a simple root, according to embodiments of the present disclosure. This filter might be unknown, so the locations of the poles are not available to us.

Figure 10:
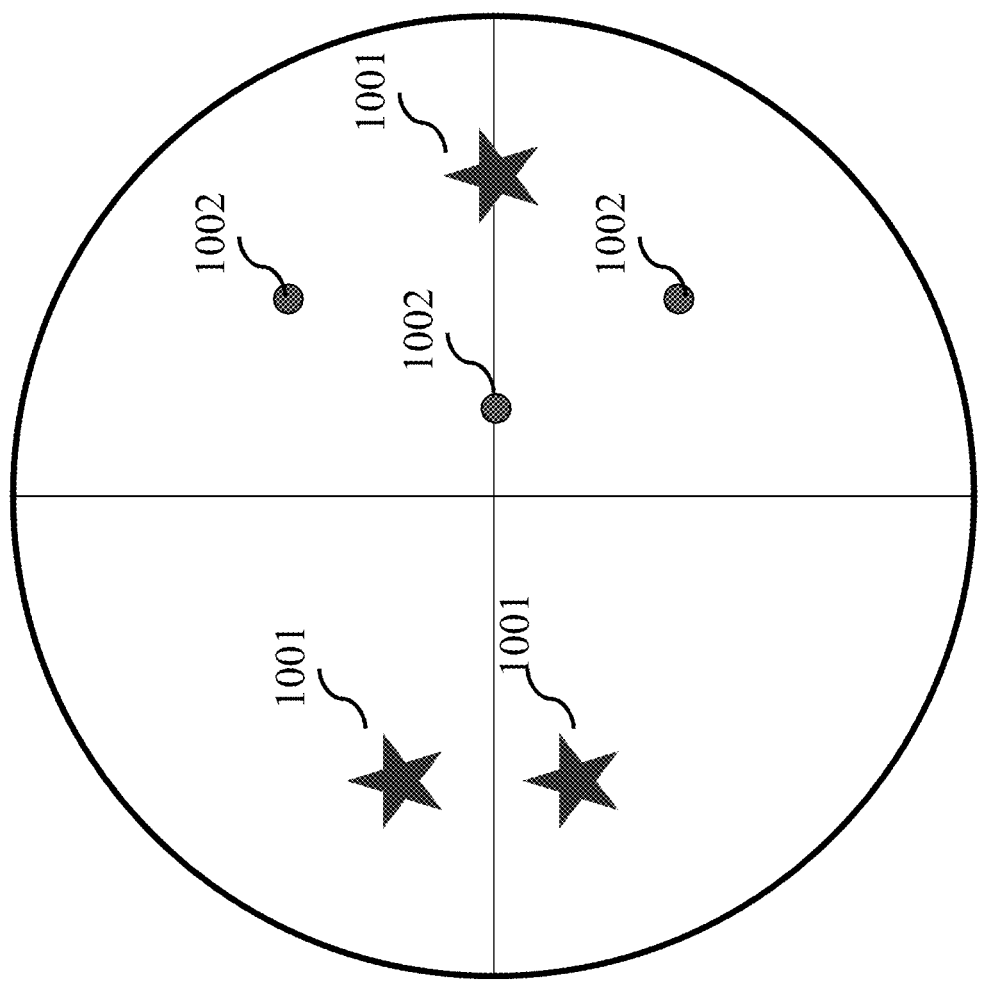
FIG. 10 is a graph illustrating an example of location of poles of an autoregressive-moving average filter with a pair of conjugate roots and a simple root as well as three poles corresponding to random projection filters, according to embodiments of the present disclosure.

FIG. 10 is a graph illustrating an example of location of poles 1001 of an unknown autoregressive-moving average filter with a pair of conjugate roots and a simple root as well as three poles 1002 corresponding to random projection filters, according to embodiments of the present disclosure. If the poles corresponding to the random projection filters are close enough to the poles of the unknown filter, their behavior would be the same.

Figure 11:
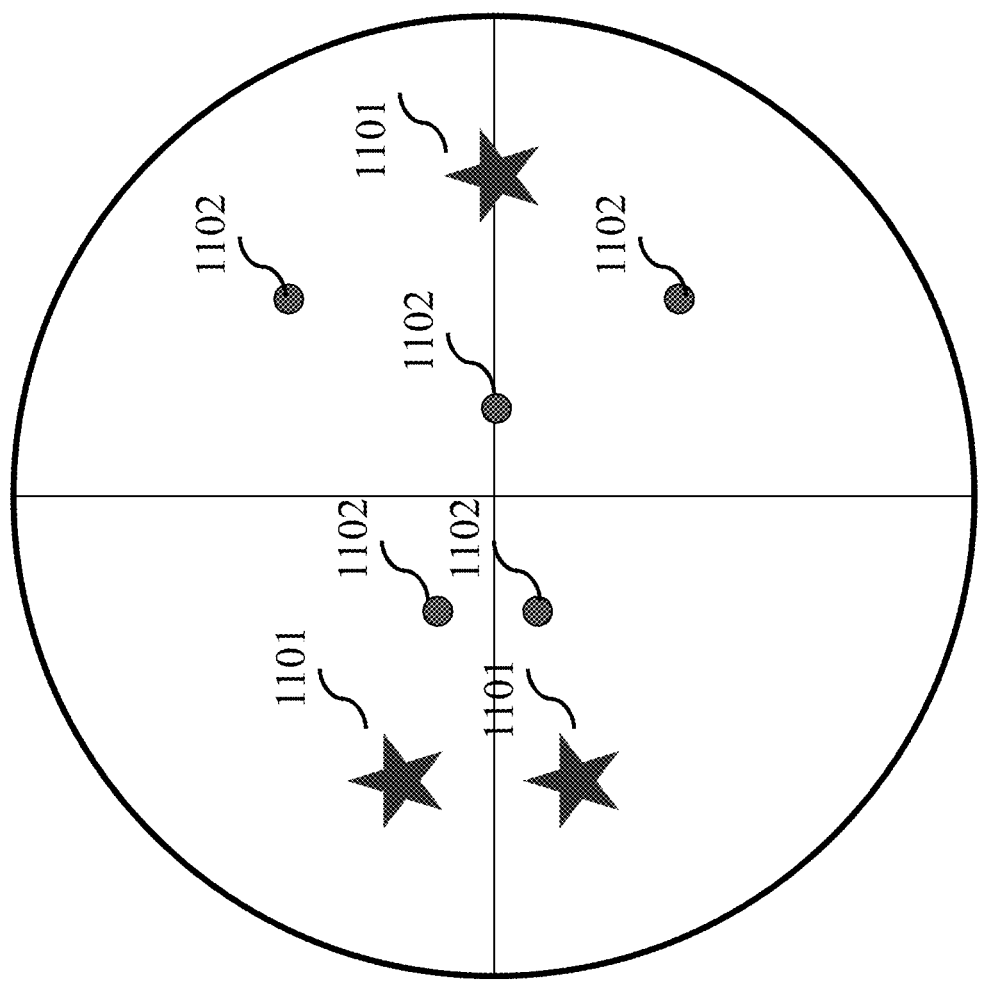
FIG. 11 is a graph illustrating an example of location of poles of an autoregressive-moving average filter with a pair of conjugate roots and a simple root as well as five poles corresponding to random projection filters, according to embodiments of the present disclosure.

FIG. 11 is similar to FIG. 10, with the difference that there are more random projection filters 1102, with poles randomly scattered around the unit circle. This figure shows that we can approximate the true, but unknown, poles 1101 better as we have more random poles scattered around.

Figure 12:
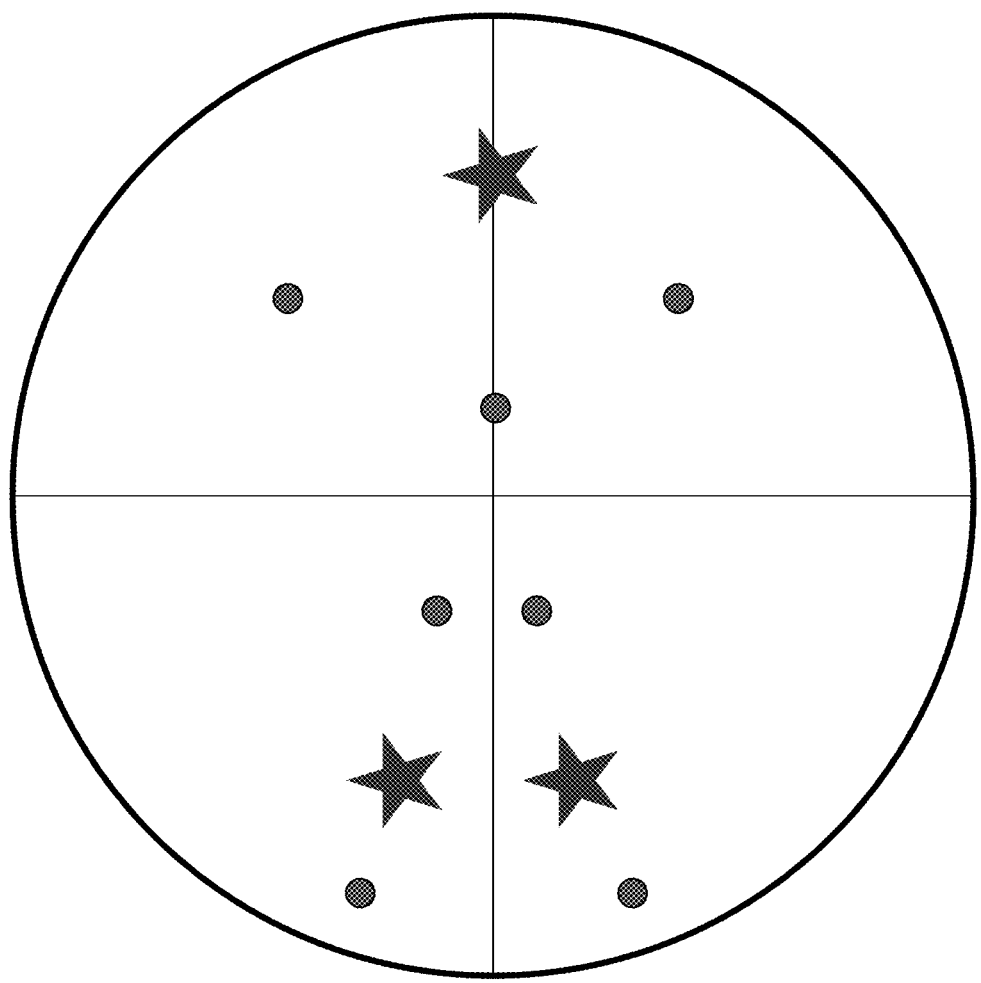
FIG. 12 is a graph illustrating an example of location of poles of an autoregressive-moving average filter with a pair of conjugate roots and a simple root as well as seven poles corresponding to random projection filters, according to embodiments of the present disclosure.
Figure 13:
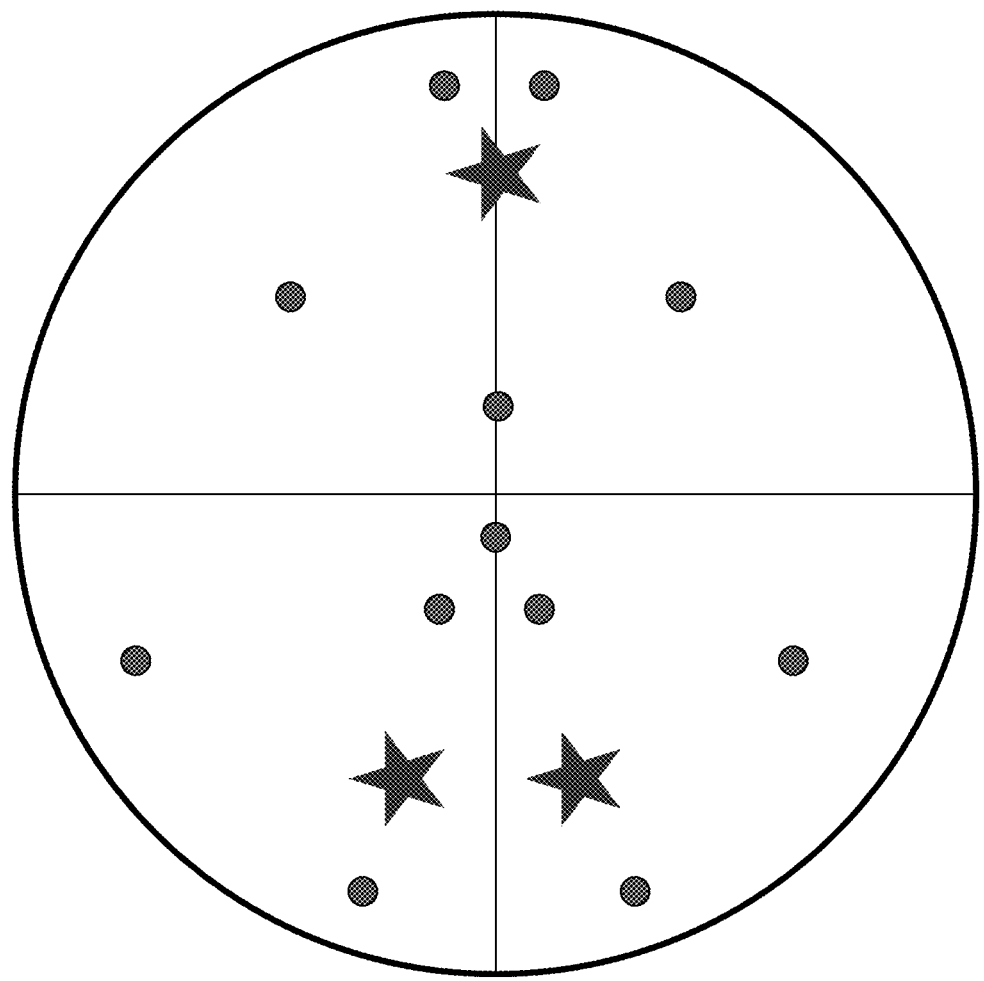
FIG. 13 is a graph illustrating an example of location of poles of an autoregressive-moving average filter with a pair of conjugate roots and a simple root as well as seven poles corresponding to random projection filters according to embodiments of the present disclosure.
Figure 14:
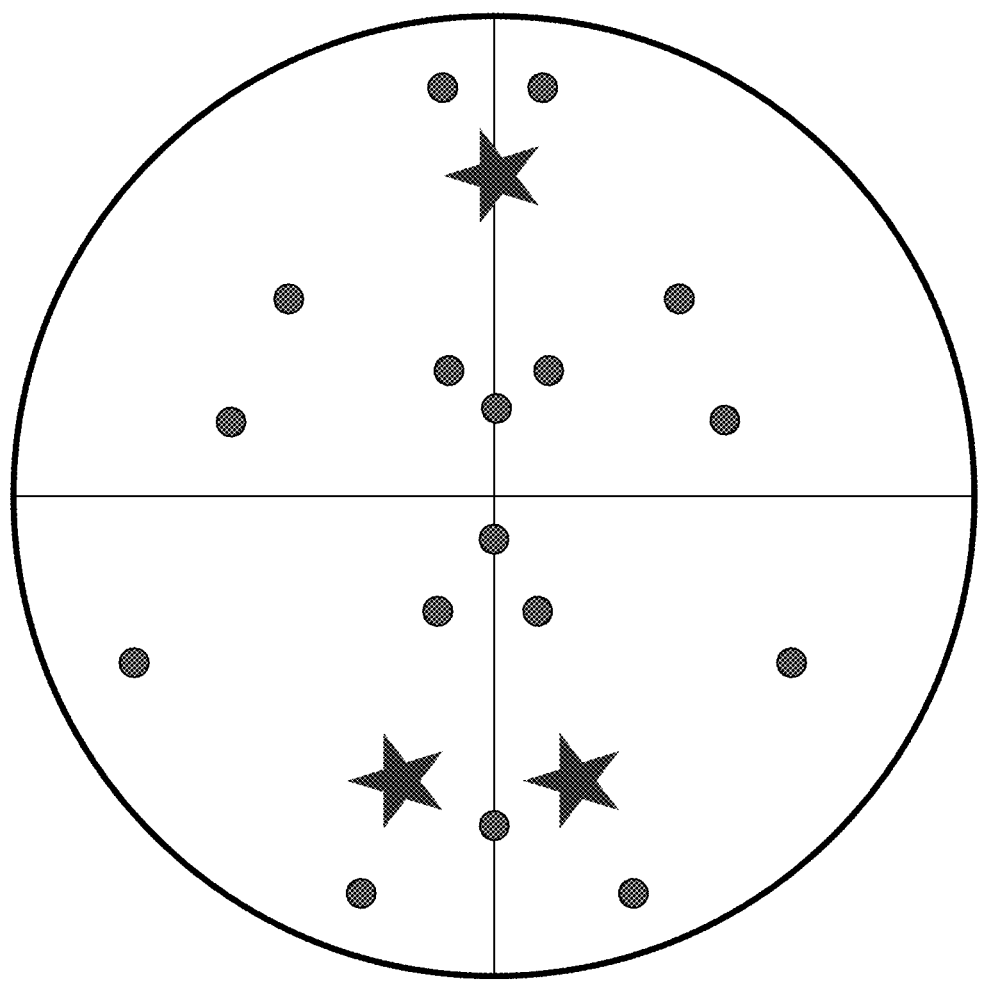
FIG. 14 is a graph illustrating an example of location of poles of an autoregressive-moving average filter with a pair of conjugate roots and a simple root as well as twelve poles corresponding to random projection filters according to embodiments of the present disclosure.

FIG. 12, FIG. 13 and FIG. 14 are graphs illustrating the same concept as FIG. 10 and FIG. 11.

Figure 15A:
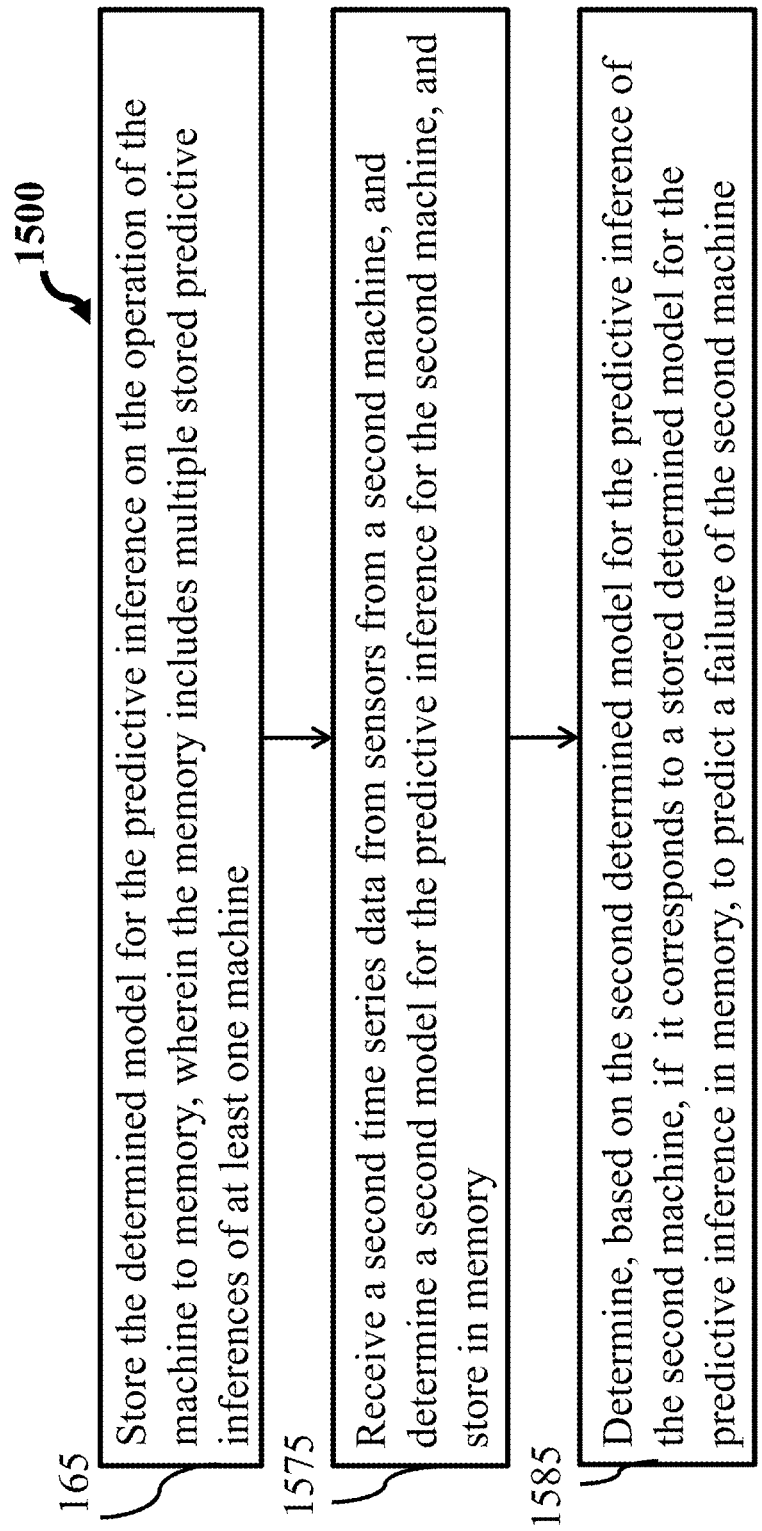
FIG. 15A is a block diagram illustrating the steps of another embodiment incorporating a second times series data from a second machine to determine a second model for a predictive inference, and using the previously stored determined models for the predictive inferences, compared to the second determined model for the predictive inference of the second machine, to predict a failure of the second machine, according to an embodiment of the present disclosure.

FIG. 15A is a block diagram illustrating the steps of another embodiment incorporating a second times series data from a second machine to determine a second model for a predictive inference. Then, using the previously stored determined models for the predictive inferences, to compare the second determined model for the predictive inference of the second machine, to predict a failure of the second machine, according to an embodiment of the present disclosure. Further, the second machine can be similar to the original machine, and each sensor of the second machine measures a same parameter as a respective sensor of the sensors of the original machine. Further still, the second time series data of the second machine can have a same period of time as the times series data of the original machine, or the second times series data of the second machine can have a same sampling rate as a regular sampling rate for the times series data of the original machine.

Figure 15B:
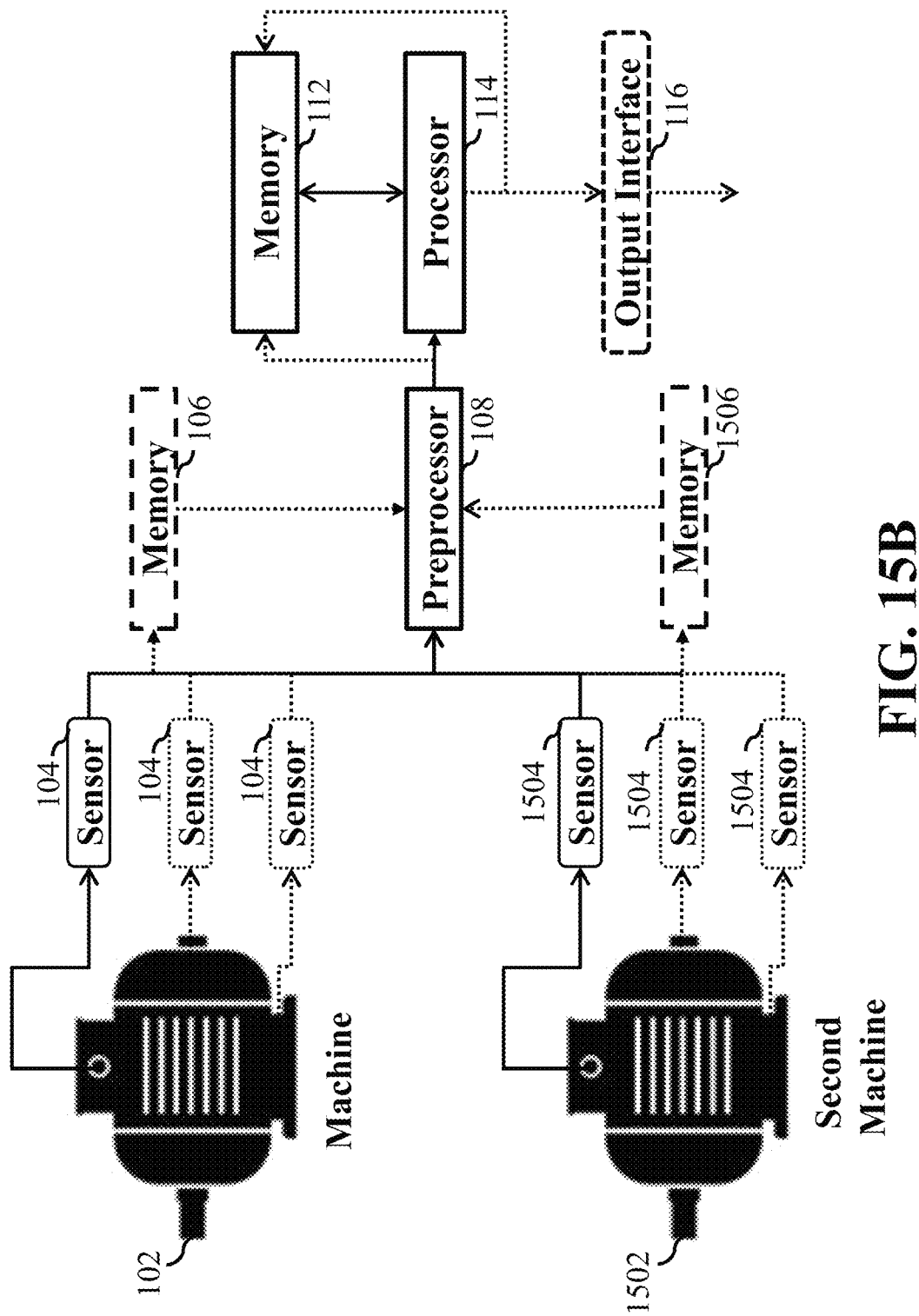
FIG. 15B is a schematic illustrating components of the system of FIG. 15A, according to an embodiment of the present disclosure.

FIG. 15B is a schematic illustrating components of the system of FIG. 15A, according to an embodiment of the present disclosure. The second machine 1502 can include sensors 1504 optionally connected to a memory 106 or directly connected to the preprocessor 108, which may be connected to memory 112. The preprocessor sends the data to processor 114 to be processed and the processed data can either be stored in memory 112 or outputted via the output interface 116.

Referring to FIG. 15A and FIG. 15B, at step 1575, the method 1500 includes receiving, by the preprocessor 108, a second times series data stream from a sensor 1504 of second machine 1502. Optionally (see FIG. 17), a user interface in communication with the computer and the computer readable memory, can acquire and stores the second times series data stream in the computer readable memory upon receiving an input from a surface of the user interface by a user.

Step 1585 includes determining based on the second determined model for the predictive inference of the second machine, if it corresponds to a stored determined models for predictive inferences in memory, to predict a failure of the second machine Specifically, whether the second determined model for the predictive inference of the second machine 1502, when compared to stored determined models for the predictive inferences in memory, can predict a failure of the second machine. It is noted that the second times series data is sampled at the same sampling rate as the stored time series data used to generate the stored determined models for the predictive patterns in memory.

FIG. 16A is a block diagram illustrating the steps of another embodiment incorporating a first time series data and a second time series data from sensors being of different types from a third machine. Then, using the previously stored determined models for the predictive inferences, compare them with the two determined models for the predictive inferences of the third machine, to predict a failure of the third machine, according to an embodiment of the present disclosure.

FIG. 16B is a schematic illustrating components of the system of FIG. 16A, according to an embodiment of the present disclosure. The third machine 1602 can include sensors 1604 optionally connected to a memory 1606 or directly connected to the preprocessor 108, which may be connected to memory 112. The preprocessor 108 sends the data to processor 114 to be processed and the processed data can either be stored in memory 112 or outputted via the output interface 116.

Referring to FIG. 16A and FIG. 16B, at step 1650 of FIG. 16A, the method 1600 includes receiving, by the preprocessor 108, a first time series data and a second time series data from sensors 1604 being of different type from the third machine 1602.

Step 1655 of FIG. 16A includes determining a first model for the predictive inference for the third machine 1602 based on the first time series data, and a second model for the predictive inference for the third machine 1602 based on the second time series data of the third machine, and store in memory 112.

Step 1660 includes predicting a failure of the third machine by taking either one of the two determined models for the predictive inferences from the first and second time series data of the two sensors from the third machine, and compares them to the stored determined models for the predictive inferences in memory.

Figure 17:
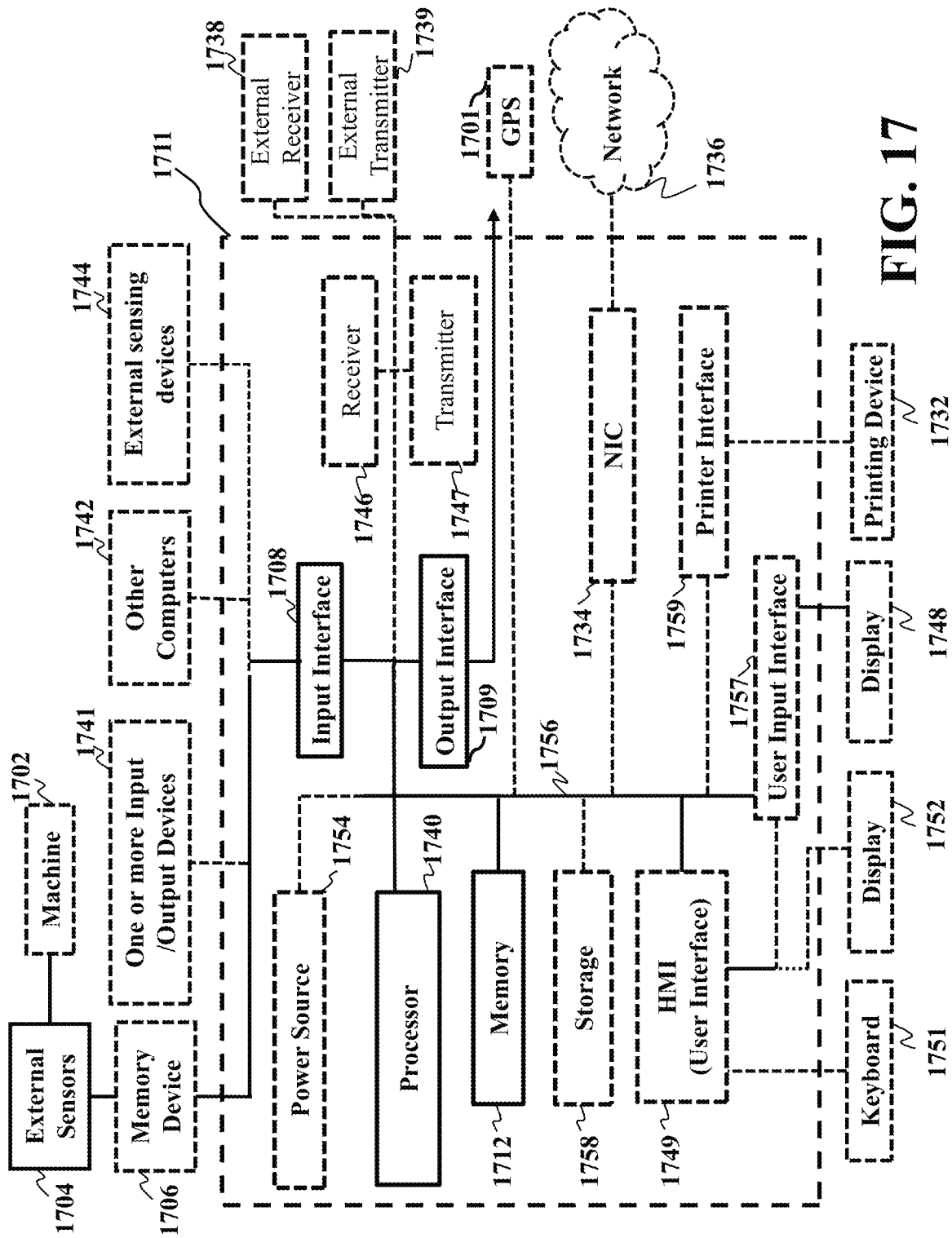
FIG. 17 is a block diagram of illustrating the method of FIG. 1A, that can be implemented using an alternate computer or processor, according to embodiments of the present disclosure.

FIG. 17 is a block diagram of illustrating the method of FIG. 1A, that can be implemented using an alternate computer or processor, according to embodiments of the present disclosure. The computer 1711 includes a processor 1740, computer readable memory 1712, storage 1758 and user interface 1749 with display 1752 and keyboard 1751, which are connected through bus 1756. For example, the user interface 1764 in communication with the processor 1740 and the computer readable memory 1712, acquires and stores the set of training data examples in the computer readable memory 1712 upon receiving an input from a surface, keyboard surface 1764, of the user interface 1764 by a user.

The computer 1711 can include a power source 1754, depending upon the application the power source 1754 may be optionally located outside of the computer 1711. Linked through bus 1756 can be a user input interface 1757 adapted to connect to a display device 1748, wherein the display device 1748 can include a computer monitor, camera, television, projector, or mobile device, among others. A printer interface 1759 can also be connected through bus 1756 and adapted to connect to a printing device 1732, wherein the printing device 1732 can include a liquid inkjet printer, solid ink printer, large-scale commercial printer, thermal printer, UV printer, or dye-sublimation printer, among others. A network interface controller (NIC) 1734 is adapted to connect through the bus 1756 to a network 1736, wherein time series data or other data, among other things, can be rendered on a third party display device, third party imaging device, and/or third party printing device outside of the computer 1711.

Still referring to FIG. 17, the time series data or other data, among other things, can be transmitted over a communication channel of the network 1736, and/or stored within the storage system 1758 for storage and/or further processing. Further, the time series data or other data may be received wirelessly or hard wired from a receiver 1746 (or external receiver 1738) or transmitted via a transmitter 1747 (or external transmitter 1739) wirelessly or hard wired, the receiver 1746 and transmitter 1747 are both connected through the bus 1756. The computer 1711 may be connected via an input interface 1708 to external sensing devices 1744 and external input/output devices 1741. For example, the external sensing devices 1744 may include sensors gathering data before-during-after of the collected time-series data of the machine. For instance, environmental conditions approximate the machine or not approximate the machine, i.e. temperature at or near machine, temperature in building of location of machine, temperature of outdoors exterior to the building of the machine, video of machine itself, video of areas approximate machine, video of areas not approximate the machine, other data related to aspects of the machine. The computer 1711 may be connected to other external computers 1742. An output interface 1709 may be used to output the processed data from the processor 1740.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine. Typically, the functionality of the program modules may be combined or distributed as desired in various embodiments.

Also, the embodiments of the present disclosure may be embodied as a method, of which an example has been provided. The acts performed as part of the method may be ordered in any suitable way. Accordingly, embodiments may be constructed in which acts are performed in an order different than illustrated, which may include performing some acts concurrently, even though shown as sequential acts in illustrative embodiments. Further, use of ordinal terms such as "first," "second," in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Although the present disclosure has been described with reference to certain preferred embodiments, it is to be understood that various other adaptations and modifications can be made within the spirit and scope of the present disclosure. Therefore, it is the aspect of the append claims to cover all such variations and modifications as come within the true spirit and scope of the present disclosure.

What is claimed is:

1. A system for managing a health of a machine based on a prediction of a state of the machine, wherein the prediction of the state of the machine is by determining a model for predictive inference on an operation of the machine, comprising:
sensors in communication with the machine to generate times series data;
an input interface to receive and store the times series data to a non-transitory computer storage medium, the times series data includes training time series data obtained at a training time and test time series data obtained at a test time, the times series data represents an operation of the machine for a period of time, wherein the training time series data includes previously determined observations labeled with an outcome of the predictive inference;
a controller;
a processor in communication with the input interface, the non-transitory computer storage medium and the controller, the processor is configured to:
access the stored times series data;
apply a set of recursive and stable filters for filtering at the training time to the training time series data, at the test time to the test time series data or both, to obtain a set of filtered time series data, such that a data point in the set of filtered time series data corresponds to an observation in the time series data that is a function of the corresponding observation and past observations in the time series data preceding the corresponding observation;
determine the model for the predictive inference using the training time series data, based on filtering the training time series data with a set of filters to produce a set of filtered training time series data, so as to obtain the determined model for the predictive inference on the operation of the machine, and store the determined model to the non-transitory computer storage medium;
output the determined model via an output interface in communication with the processor, to the controller; and
receive the determined model by the controller, wherein the controller provides a diagnosis of faults or an estimated remaining life span of the machine to manage the health of the machine, according to the determined model for the predictive inference on the operation of the machine.

2. The system of claim 1, wherein the training includes:
forming an informational vector with data points from different filtered time series data obtained from the sensors observing the machine from the training time series data; and
training the model using a machine learning algorithm using the informational vector as its input.

3. The system of claim 1, wherein each filter in the set of filters is processed in parallel with other filters in the set of filters by the processor that are stored in the non-transitory computer storage medium.

4. The system of claim 1, wherein the set of filters are random projection filters and they collectively define a random projection filter bank.

5. The system of claim 4, wherein the random projection filters includes a set of autoregressive filters with randomly chosen parameters that receives the time series data as an input, then outputs an output of an information vector.

6. The system of claim 4, wherein the time series data is processed by each filter in the set of filters in the random projection filter bank, and generates an output from each filter in the set of filters of the random projection filter bank, such that the output of each filter is in a form of a time series, wherein if additional time series data is accessed at a later time, the output time series also changes.

7. The system of claim 1, wherein a number of filters selected from the set of filters is selected based on hardware limitations of the non-transitory computer storage medium and hardware limitations of the processor, and in combination with a model selection procedure that is based on a quality of the prediction of the predictive inference model.

8. The system of claim 1, wherein a number of filters in the set of filter is dependent upon a function of a maximum number of filters capable of being processed based on a hardware capacity of the non-transitory computer storage medium and hardware processing limitations of the processor, and an exact number of filters required for optimizing a quality of the prediction of the model of the predictive inference that is based on the model selection.

9. The system of claim 1, wherein the processor determines the set of filters by randomly choosing a set of numbers that define a set of randomly selected stable and recursive filters, such that the recursive filters include auto regressive filters and non-auto regressive filters, and the stable filters include non-divergent filters.

10. The system of claim 1, wherein the recursive filter includes a software module with internal states stored in the non-transitory computer storage medium, and receives the time series data as an input, then outputs a value based on the internal state of the software module and the received input, and updates the non-transitory computer storage medium.

11. The system of claim 1, wherein the stable filter includes a rational polynomial, wherein a denominator of the rational polynomial is a polynomial with roots that are either real or complex, such that a magnitude of the roots is equal to or smaller than one.

12. The system of claim 1, wherein the model is a machine learning model, such that the set of filters are random projection filters and the machine learning model includes a regression estimator, a classifier, or a density estimator, that act on a vector given by an output of the random projection filters.

13. The system of claim 1, wherein the predictive inference is from the group consisting of one of: a time series prediction; an estimate of remaining useful lifetime for the purpose of fault prognosis; fault recognition and detection; fault diagnosis; or other machine learning tasks that benefit from a summary of the time series data.

14. The system of claim 1, wherein the set of filters is a random projection filter bank and the random projection filter bank processes the time series data and provides a vector that approximately summarizes the time series data, wherein an output of the random projection filter bank describes a low-dimensional dynamical system having a dimension smaller than a dimension of the vector describing the time series.

15. The system of claim 1, wherein the set of filters is a random projection filter bank and the random projection filter bank includes a multitude of stable random projection filters, wherein each random projection filter is a stable autoregressive-moving average filter that is described by numerator polynomials and denominator polynomials with randomly chosen poles and zeros, wherein the poles are roots of the denominator's polynomial and the zeros are roots of the numerator's polynomial.

16. The system of claim 1, wherein a user interface in communication with the processor and the non-transitory computer storage medium, acquires and stores the time series data in the non-transitory computer storage medium upon receiving an input from a surface of the user interface by a user, so the time series data is capable of being accessed by the processor.

17. A non-transitory computer readable storage medium embodied thereon a program executable by a computer for performing a method, the method is for managing a health of a machine based on a prediction of a state of the machine, wherein the prediction of the state of the machine is by determining a model for predictive inference on an operation of the machine, the steps comprising:

using stored times series data generated by sensors in communication with the machine from the non-transitory computer storage medium, such that the times series data includes training time series data obtained at a training time and test time series data obtained at a test time, wherein the times series data represents the operation of the machine for a period of time, and the training time series data includes observations labeled with an outcome of the predictive inference;

applying a set of recursive and stable filters for filtering at a training time to the training time series data, at a test time to the test time series data or both, to obtain a set of filtered time series data, such that a data point in the set of filtered time series data corresponds to an observation in the time series data that is a function of the corresponding observation and past observations in the time series data preceding the corresponding observation, wherein the filtering at the training time uses the training times series data for the filtering and the filtering at the test time uses the test time series data for the filtering;

determining the model for the predictive inference using the training time series data, based on filtering the training time series data with a set of filters to produce a set of filtered training time series data, so as to obtain the determined model for the predictive inference on the operation of the machine, and store the determined model to the non-transitory computer storage medium;

outputting the determined model to a controller via an output interface; and receiving the determined model by the controller, wherein the controller provides a diagnosis of faults or an estimated remaining life span of the machine to manage the health of the machine, according to the determined model for the predictive inference on the operation of the machine, wherein the determined model for the predictive inference assists in recognizing the health of the machine, a type of fault of the machine or a remaining useful life of the machine, wherein the steps of the method are implemented using a processor in communication with the non-transitory computer storage medium, the output interface and the controller.

18. The non-transitory computer readable storage medium of claim 17, wherein the times series data is accessed by an input interface in communication with the processor, and the test time series data is used as training time series data when conditions are set forth for solving for the respective predictive inference, or by a user input.

19. A method for managing a health of a machine based on a prediction of a state of the machine, wherein the prediction of the state of the machine is by determining a machine learning model for predictive inference on an operation of the machine, the steps comprising:

accessing stored times series data generated by sensors in communication with the machine from a computer readable memory, such that the times series data includes training time series data obtained at a training time and test time series data obtained at a test time, wherein the times series data represents an operation of the machine for a period of time, and the training time series data includes observations labeled with an outcome of the predictive inference;

applying a set of recursive and stable filters for filtering at the training time to the training time series data, at the test time to the test time series data or both, to obtain a set of filtered time series data, such that a data point in the set of filtered time series data corresponds to an observation in the time series data that is a function of the corresponding observation and past observations in the time series data preceding the corresponding observation, wherein the filtering at the training time uses the training time series data for the filtering and the filtering at the test time uses the test time series data for the filtering;

determining the machine learning model for the predictive inference using the training time series data, based on filtering the training time series data with a set of filters to produce a set of filtered training time series data, so as to obtain the determined machine learning model for the predictive inference on the operation of the machine, and store the determined machine learning model to the computer readable memory;

outputting the determined model to a controller via an output interface; and receiving the determined model by the controller, wherein the controller provides a diagnosis of faults or an estimated remaining life span of the machine to manage the health of the machine, according to the determined machine learning model for the predictive inference on the operation of the machine, wherein the steps of the method are implemented using a processor in communication with the computer readable memory, the output interface and the controller.

\* \* \* \* \*